(12) United States Patent
Jang et al.

(10) Patent No.: US 12,394,503 B2
(45) Date of Patent: Aug. 19, 2025

(54) METHOD FOR PREDICTING THE MELTING TEMPERATURE OF OLIGONUCLEOTIDE

(71) Applicant: SEEGENE, INC., Seoul (KR)

(72) Inventors: Mi Hyun Jang, Seoul (KR); Han Bit Lee, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 1078 days.

(21) Appl. No.: 17/050,030

(22) PCT Filed: Jun. 28, 2019

(86) PCT No.: PCT/KR2019/007908
§ 371 (c)(1),
(2) Date: Oct. 23, 2020

(87) PCT Pub. No.: WO2020/005019
PCT Pub. Date: Jan. 2, 2020

(65) Prior Publication Data
US 2021/0074383 A1    Mar. 11, 2021

(30) Foreign Application Priority Data
Jun. 29, 2018 (KR) .......................... 10-2018-0075939

(51) Int. Cl.
*G16B 40/00* (2019.01)

(52) U.S. Cl.
CPC ....... *G16B 40/00* (2019.02); *C12Q 2527/107* (2013.01)

(58) Field of Classification Search
CPC .......................... G16B 40/00; C12Q 2527/107
See application file for complete search history.

(56) References Cited

U.S. PATENT DOCUMENTS

| | | |
|---|---|---|
| 8,055,451 B2 | 11/2011 | Owczarzy et al. |
| 9,081,737 B2 | 7/2015 | Behlke et al. |
| 2010/0233687 A1 | 9/2010 | Cao |

OTHER PUBLICATIONS

Dumousseau, Marine, et al. "MELTING, a flexible platform to predict the melting temperatures of nucleic acids." BMC bioinformatics 13 (2012): 1-12. (Year: 2012).*
Santalucia, John. "Physical principles and visual-OMP software for optimal PCR design." PCR primer design (2007): 3-33. (Year: 2007).*

(Continued)

*Primary Examiner* — Olivia M. Wise
*Assistant Examiner* — Mary C Leverett
(74) *Attorney, Agent, or Firm* — Harness, Dickey & Pierce, P.L.C.

(57) ABSTRACT

The present invention relates to a method for predicting the melting temperature ($T_m$) of an oligonucleotide, in particular a primer or probe, in a PCR or hybridization assay. The method of present invention can accurately predict the $T_m$ of an oligonucleotide in various reaction environments using the equations for $T_m$ calculation, the equation including parameter values optimized for the reaction environment in which the oligonucleotide is to be used.

9 Claims, 4 Drawing Sheets

(56) References Cited

OTHER PUBLICATIONS

Panjkovich, Alejandro, and Francisco Melo. "Comparison of different melting temperature calculation methods for short DNA sequences." Bioinformatics 21.6 (2005): 711-722. (Year: 2005).*
Allawi, Hatim T., and John SantaLucia. "Nearest Neighbor Thermodynamic Parameters for Internal G-A Mismatches in DNA." Biochemistry 37.8 (1998): 2170-2179. (Year: 1998).*
Breslauer et al., Proc. Natl. Acad. Sci. USA 1986, 83: 3746-3750.
Santa Lucia et al., Biochemistry 1996, 35: 3555-3562.
Sugimoto et al., Nuc Acids Res 1996, 24: 4501-4505.
Chen, H. et al., Biotechniques, 1997, vol. 22, No. 6, pp. 1158-1160.
Allawi et al., Biochemistry 1997, 36: 10581-10594.
Santa Lucia, Proc. Natl. Acad. Sci. USA 1998, 95: 1460-1465.
Santa Lucia et al., Annu. Rev. Biophys. Biomol. Struct. 2004. 33: 415-440.
Weber, G., Bioinformatics, 2015, vol. 31, No. 6, pp. 871-877.
International Search Report from corresponding PCT Application No. PCT/KR2019/007908, dated Oct. 24, 2019.

* cited by examiner (a)

(a)

(a)

(b)

(a)

(b)

METHOD FOR PREDICTING THE MELTING TEMPERATURE OF OLIGONUCLEOTIDE

CROSS-REFERENCE TO RELATED APPLICATIONS

This application is a national phase application of PCT Application No. PCT/KR2019/007908, filed on Jun. 28, 2019, which claims priority to Korean Patent Application No. 10-2018-0075939, filed on Jun. 29, 2018. The entire disclosures of the applications identified in this paragraph are incorporated herein by references.

FIELD OF THE INVENTION

The present invention relates to a method for predicting the melting temperature of an oligonucleotide, particularly a primer or probe in a PCR or hybridization assay.

BACKGROUND OF THE INVENTION

Hybridization between complementary nucleic acids is one of the important features in the Watson-Crick Model for DNA structure and is used in many biological and biomedical fields. For example, a method of replicating or amplifying a nucleic acid molecule is initiated by the step of hybridizing a complementary oligonucleotide (typically, a primer) to a specific site of a target nucleic acid molecule. Then, a polymerase uses the target nucleic acid molecule as a template to synthesize a complementary nucleic acid from the primer.

A method known as polymerase chain reaction (PCR) has been widely used in the biological and biomedical fields. In PCR, two or more primers that hybridize to different sites of the target nucleic acid are used. The target nucleic acid sequence and its complement are then amplified through multiple cycles of heating and cooling to repeatedly hybridize and dissociate complementary strands. The amplification allows a small amount of target nucleic acid to be used for detection, sequencing, and the like.

Multiplex PCR is a modification of PCR that uses multiple pairs of primers in a single PCR mixture to amplify and detect a plurality of nucleic acids in a sample. This technique allows for simultaneous amplification and evaluation of multiple different target nucleic acids in a sample. However, successful multiplex PCR is not attainable due to the difficulty in selection and design of suitable oligonucleotides.

Another technique widely used in the biological and biomedical fields employs nucleic acid hybridization to detect a target nucleic acid sequence in a sample. Such technique, for example, Southern blotting and the like, immobilizes target nucleic acid molecules in a sample on a solid surface or support (e.g., a membrane support). The immobilized target nucleic acid molecule is hybridized with one or more complementary nucleic acids (referred to as probes) and detected by measuring a signal from a detectable label on the probe.

The success of such techniques including nucleic acid hybridization depends on the use of primers and probes that specifically hybridize to the target nucleic acid molecule. This is particularly critical in multiplex PCR involving more oligonucleotides.

The stability of oligonucleotides such as primers or probes is often expressed as the melting temperature ($T_m$) of the duplex between an oligonucleotide and its complementary strand. The $T_m$ is defined as the temperature at which half of the duplex will dissociate to become single-stranded. Preferably, the nucleic acid hybridization is carried out at a temperature slightly lower than $T_m$ to optimize hybridization between the primer or probe and its target nucleic acid and minimize non-specific hybridization of the primer or probe to the non-target nucleic acid. The $T_m$ is also important in PCR involving thermal cycling.

Conventionally, various methods for predicting the $T_m$ of a specific oligonucleotide have been proposed.

Marmur and Doty (1962) used a rather simple formula where the $T_m$ depends only on the relative content of cytosine and guanine. This formula was later improved by adding a correction factor which is also responsible for salt concentration, thus adjusting the $T_m$ value for different experimental conditions (Wetmur, 1991). An indepth analysis of DNA oligonucleotides and their corresponding experimental $T_m$s has led to the conclusion that not only the relative amounts of cytosine and guanine concentrations determine the thermal denaturation of DNA, but also the sequential arrangement of different nucleotides in DNA sequences were found to play a major role in the experimental value of $T_m$s. Later, Breslauer et al. (Proc. Natl. Acad. Sci. USA 1986, 83: 3746-3750) adopted a $T_m$ prediction model known as the "nearest-neighbor (NN)" model (SantaLucia et al., Biochemistry 1996, 35: 3555-3562; Santa Lucia, Proc Natl Acad Sci USA 1998, 95: 1460-1465). The NN model uses nearest-neighbor thermodynamic parameters and several optimized NN tables with NN parameters have been published (Gotoh and Tagashira, 1981; Vologodskii et al., 1984; Breslauer et al., 1986; Delcourt and Blake, 1991; Doktycz et al., 1992; SantaLucia et al., 1996; Sugimoto et al., 1996; Allawi and Santa Lucia, 1997).

The NN models use the values of the NN parameters obtained under a fixed reaction environment (e.g., 1M NaCl). However, the reaction environment in which oligonucleotides for $T_m$ prediction are tested may vary widely. Therefore, the use of the NN parameter values optimized for a fixed reaction environment may lead to inaccurate prediction of the $T_m$s of oligonucleotides, because such values do not accurately reflect all the various reaction environments.

In order to address the issue, there has been proposed a method of using a certain correction factor (such as a correction factor related to salt concentration) in addition to the NN parameters. However, since the $T_m$ of the oligonucleotide is also affected by many other factors and it is difficult to establish the formula for $T_m$ calculation considering all of these correction factors, the approach using a correction factor is also not suitable for predicting an accurate $T_m$ that reflects the entire reaction environment. Further, the above method assumes that the values of the NN parameters for each NN sequence (also referred to as NN propagation) do not change for all reaction environments, except for the value of the correction factor. However, since such changes in the reaction environment also affect the values of the thermodynamic NN parameters for each NN sequence, the above approach has limitations in accurately predicting the $T_m$ of the oligonucleotide in various reaction environments.

Therefore, there is still a need to develop a novel method for accurately predicting the $T_m$ of an oligonucleotide in a variety of reaction environments.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have endeavored to develop a method for accurately predicting the melting temperature ($T_m$) of an oligonucleotide of interest in various reaction environments. As a result, the present inventors have established an equation for $T_m$ calculation for each of the differently defined reaction environments, using a plurality of reference data sets, each comprising information about the sequences of a plurality of reference oligonucleotides and information about the experimental $T_m$s of the plurality of reference oligonucleotides in a defined reaction environment, and have confirmed that the use of the equation for $T_m$ calculation allows for accurate prediction of the $T_m$ of an oligonucleotide of interest in various reaction environments.

Accordingly, it is an object of the present invention to provide a method for predicting the $T_m$ of an oligonucleotide.

It is another object of the present invention to provide a computer readable storage medium containing instructions to configure a processor to perform a method for predicting the $T_m$ of an oligonucleotide.

It is still another object of the present invention to provide an apparatus for predicting the $T_m$ of an oligonucleotide.

Other objects and advantages of the present invention will become apparent from the detailed description to follow taken in conjugation with the appended claims and drawings.

DETAILED DESCRIPTION OF THIS INVENTION

I. Method for Predicting the Melting Temperature ($T_m$) of an Oligonucleotide in Differently Defined Reaction Environments In a first aspect of this invention, there is a method for predicting the melting temperature ($T_m$) of an oligonucleotide of interest, comprising the steps of:

(a) providing a plurality of reference data sets, wherein the reference data set comprises (i) information about the sequences of a plurality of reference oligonucleotides and (ii) information about the experimental $T_m$s of the plurality of reference oligonucleotides in a defined reaction environment, wherein the plurality of reference data sets are generated in differently defined reaction environments;

(b) establishing an equation for $T_m$ calculation for each of the differently defined reaction environments using each of the plurality of reference data sets including the information (i)-(ii); wherein the establishment of the equation comprises determining the values of the parameters in the equation, wherein the parameters comprise nearest-neighbor (NN) thermodynamic parameters; and (c) calculating the $T_m$ of an oligonucleotide of interest in one among the differently defined reaction environments using the equation established for the one among the differently defined reaction environments.

The present inventors have endeavored to develop a method for accurately predicting the melting temperature ($T_m$) of an oligonucleotide of interest in various reaction environments. As a result, the present inventors have established an equation for $T_m$ calculation for each of the differently defined reaction environments, using a plurality of reference data sets, each comprising information about the sequences of a plurality of reference oligonucleotides and information about the experimental $T_m$s of the plurality of reference oligonucleotides in a defined reaction environment, and have confirmed that the use of the equation for $T_m$ calculation allows for accurate prediction of the $T_m$ of an oligonucleotide of interest in various reaction environments.

The $T_m$ prediction of the present invention is based on a nearest-neighbor (NN) model using thermodynamic nearest-neighbor parameters. Nearest-neighbor model-based $T_m$ prediction is well known in the art (see Breslauer et al., Proc. Natl. Acad. Sci. U.S.A. 1986, 83: 3746-3750; Santa Lucia et al., Biochemistry 1996, 35: 3555-3562; Santa Lucia, Proc. Natl. Acad. Sci. U.S.A. 1998, 95: 1460-1465, which are incorporated herein by reference in their entirety).

Figure 1:
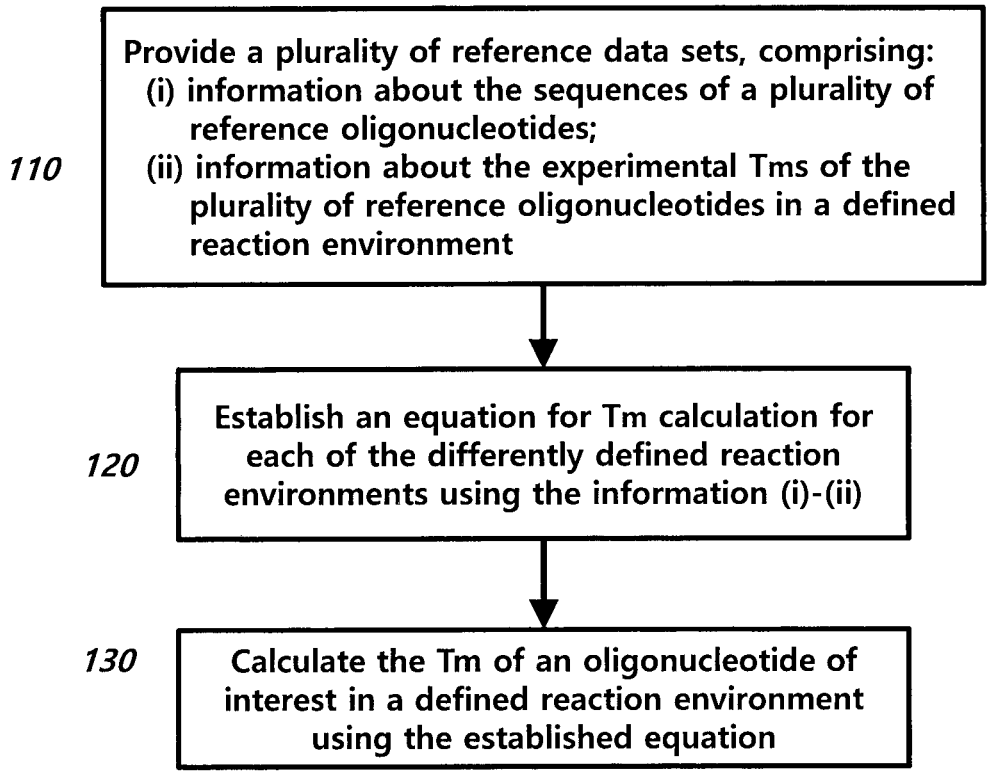
FIG. 1 shows a flow diagram illustrating a method in accordance with an embodiment of the present invention.

FIG. 1 shows a flow diagram illustrating each step of a method 100 in accordance with an embodiment of the present invention. The method of the present invention will now be described with reference to FIG. 1.

Step (a): Providing a Plurality of Reference Data Sets 110

First, a plurality of reference data sets is provided 110. The reference data set comprises (i) information about the sequences of a plurality of reference oligonucleotides and (ii) information about the experimental $T_m$s of the plurality of reference oligonucleotides in a defined reaction environment, wherein the plurality of reference data sets are generated in differently defined reaction environments.

The term "oligonucleotide" as used herein refers to a linear oligomer of natural or modified monomers or linkages, including deoxyribonucleotides, ribonucleotides and the like, capable of specifically hybridizing with a target nucleotide sequence, whether occurring naturally or produced synthetically. The oligonucleotide is preferably single stranded for maximum efficiency in hybridization. Preferably, the oligonucleotide is an oligodeoxyribonucleotide. The oligonucleotide of this invention can be comprised of naturally occurring dNMP (i.e., dAMP, dGM, dCMP and dTMP), nucleotide analogs, or nucleotide derivatives. The oligonucleotide can also include ribonucleotides. For example, the oligonucleotide of this invention may include nucleotides with backbone modifications such as peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The oligonucleotide as used herein is generally less than 200 nucleotides, particularly less than 150 nucleotides, more particularly less than 100 nucleotides, still more particularly less than 50 nucleotides and most particularly less than 30 nucleotides in length.

The oligonucleotides as used herein can be classified into two categories: (i) oligonucleotide whose $T_m$ is to be predicted; (ii) oligonucleotide which is used to determine the parameter values included in an equation for $T_m$ calculation in a defined reaction environment.

As used herein, the term "oligonucleotide whose $T_m$ is to be predicted" refers to an oligonucleotide having no experimental $T_m$, i.e., an oligonucleotide whose $T_m$ is unknown. The oligonucleotide is one whose $T_m$ information is required for an optimized reaction in PCR, hybridization assay and the like. The oligonucleotide may be referred to herein as "oligonucleotide of interest", or "unknown oligonucleotide".

On the other hand, the term "oligonucleotide used in the calculation of the parameter values included in an equation for $T_m$ calculation" refers to an oligonucleotide having an experimental (experimentally determined) $T_m$ in a defined reaction environment. The oligonucleotide serves to provide information about its sequence as well as information about its $T_m$ to determine the parameter values in a defined reaction environment. The oligonucleotide may be referred to herein as "reference oligonucleotide", "learning oligonucleotide" or "benchmark oligonucleotide".

As used herein, the term "reference data set" refers to a data set that contains information used to establish a nearest-neighbor (NN) model, specifically an equation for $T_m$ calculation, optimized for a defined reaction environment. The reference dataset is used to establish an NN model in a defined reaction environment and then to calculate the $T_m$ of an oligonucleotide of interest in the defined reaction environment.

As used herein, the term "a plurality of reference data sets" means at least two reference data sets. In one embodiment, a plurality of reference data sets comprises 2, 3, 4, 5, 6, 7, 8, 9, 10, or more reference data sets.

The reference data set as provided in this step is generated in a defined reaction environment. The reference data set as provided in this step may be generated by preparing a plurality of reference oligonucleotides of varying lengths and sequences and determining their experimental $T_m$s.

The plurality of reference data sets are generated in differently defined reaction environments. For example, a first reference data set is generated in a first defined reaction environment and a second reference data set is generated in a second defined reaction environment; wherein the first defined reaction environment is different from the second defined reaction environment.

The reference data set corresponds to a defined reaction environment, and the plurality of reference data sets corresponds to differently defined reaction environments.

In other words, each reference data set is used herein to establish an NN model in each reaction environment and to calculate the $T_m$ of an oligonucleotide of interest in each reaction environment, and the plurality of reference data sets is used to establish several NN models in differently defined reaction environments and to calculate the $T_m$ of an oligonucleotide of interest in the differently defined reaction environments.

The number of reference data sets corresponds to the number of the differently defined reaction environments. For example, three reference data sets correspond to three differently defined reaction environments.

Each of the reference data sets herein may be referred to as a first reference data set, a second reference data set, or the like, for identification. In this case, the first reference data set is provided to establish an equation for $T_m$ calculation having the parameter values optimized for a first defined reaction environment, and the second reference data set is provided to establish an equation for $T_m$ calculation having the parameter values optimized for a second defined reaction environment.

The reference data set comprises (i) information about the sequences of a plurality of reference oligonucleotides and (ii) information about the experimental $T_m$s of the plurality of reference oligonucleotides in a defined reaction environment. The reference data set may further comprise other information, and the information may be used to establish an equation for $T_m$ calculation. The components included in the reference data set will be described in detail.

(i) Information about the Sequences of a Plurality of Reference Oligonucleotides Each reference data set includes information about the sequences of a plurality of reference oligonucleotides. The term "information about the sequences of a plurality of reference oligonucleotides" means information derived from the nucleic acid sequences of a plurality of reference oligonucleotide molecules.

In one embodiment, the information about the sequences of a plurality of reference oligonucleotides comprises linear orders of a plurality of reference oligonucleotides.

In one embodiment, the information about the sequences of a plurality of reference oligonucleotides comprises nearest-neighbor (NN) sequences derived from a plurality of reference oligonucleotides.

In one embodiment, the information about the sequences of a plurality of reference oligonucleotides comprises the frequency for each of nearest-neighbor (NN) sequences derived from a plurality of reference oligonucleotides.

In one embodiment, the information about the sequences of a plurality of reference oligonucleotides comprises the length of a plurality of reference oligonucleotides.

In one embodiment, the information about the sequences of a plurality of reference oligonucleotides comprises the content of A, T(U), G, C, or a combination thereof in a plurality of reference oligonucleotides.

The number of the sequences of the reference oligonucleotides included in each reference data set is not particularly limited, as long as all the values of the thermodynamic parameters for the nearest-neighbor (NN) sequences (also referred to as NN propagation, preferably a total of 10 NN sequences) can be determined using the sequences of the reference oligonucleotides. The number of the sequences of the reference oligonucleotides included in each reference data set is preferably as large as possible for accurate determination of the NN parameter values, but it may be adjusted to reduce the time required for determination of the NN parameter values, and the like. For example, the number of the sequences of the reference oligonucleotides in each reference data set may be at least 20, at least 30, or at least 50, up to 100, up to 300, up to 500, up to 1000, up to 3000, or 5000.

The sequences of the reference oligonucleotides constituting each reference data set may be the same or different for each reference data set.

In one embodiment, the sequences of the reference oligonucleotides in the first reference data set is totally identical to those in the second reference data set (the reaction environment in which the $T_m$s of the reference oligonucleotides in the first reference data set are measured is different from that in which the $T_m$s of the reference oligonucleotides in the second reference data set is measured).

In another embodiment, the sequences of the reference oligonucleotides in the first reference data set is partially identical to those in the second reference data set (the reaction environment in which the $T_m$s of the reference oligonucleotides in the first reference data set are measured is different from that in which the $T_m$s of the reference oligonucleotides in the second reference data set is measured).

In still another embodiment, the sequences of the reference oligonucleotides in the first reference data set is totally different from those in the second reference data set (the reaction environment in which the $T_m$s of the reference oligonucleotides in the first reference data set are measured is different from that in which the $T_m$s of the reference oligonucleotides in the second reference data set is measured).

The sequences of a plurality of reference oligonucleotides in one reference data set may be used to construct another reference data set.

(ii) Information about the Experimental $T_m$s of the Plurality of Reference Oligonucleotides in a Defined Reaction Environment Each reference data set includes information about the experimental $T_m$s of the plurality of reference oligonucleotides in a defined reaction environment. Since each reference data set includes not only sequences of reference oligonucleotides but also their experimental $T_m$s as components, the identity between two reference data sets is determined in consideration of the two components.

As used herein, the term "experimental melting temperatures of a plurality of reference oligonucleotides in a defined reaction environment" refers to an experimental measure of melting temperature of each of the reference oligonucleotides in a defined reaction environment.

As used herein, the term "reaction environment" refers to one in which the oligonucleotide whose $T_m$ is to be predicted (oligonucleotide of interest) is used/placed/applied. In other words, the term "reaction environment" refers to the medium, particularly chemical characteristics, surrounding an oligonucleotide. The reaction environment may be defined by the types and concentrations of the components used in a reaction except the oligonucleotide of interest. For example, when an oligonucleotide whose $T_m$ is to be predicted is used in a PCR reaction, examples of the components can be used in the reaction include, without limitation, a buffers (for pH adjustment) such as Tris, Tricine, bis-Tricine, HEPES, EPPS, CHES and CAPSO; monovalent ions such as KCl, $(NH_4)_2SO_4$, NaCl, LiCl, $NH_4Cl$, $NaN_3$, $CoCl_2$, KOAc, KSO4, $(Mn(OAc)_2$ and NaOAc; divalent ions such as $MgCl_2$, $MgSO_4$, $MgSO_4$, and $ZnCl_2$; stabilizers such as BSA and gelatin; proteins such as T4 gene 32 protein and Et SSB; non-ionic detergents such as NP-40, Tween20, Triton X-100, Triton X-114, CHAPSO, IGEPAL, CHAPS, MEGA-8, Brij 35 and BRIJ 58; reducing agents such as DTT, b-mercaptoethanol and TCEP; compatible solutes such as glycerol, trehalose, sucrose, xylitol, melezitose, xylene cyanol, mannose, sorbitol, mannitol, betaine, ectoine and proline; sulfoxides such as DMSO; amides such as formamide; tetraalkyl-ammonium salts such as TMAC and TMAA; polyhydroxyl alcohols such as propylene glycol and polyvinyl alcohol (PVA); chelating agents such as EDTA and EGTA; enzymes such as polymerases, dNTPs, and the like.

The plurality of reference data sets are generated in differently defined reaction environments.

The term of "differently defined reaction environments" means that types and/or concentrations of any component used in a reaction except the oligonucleotide of interest is different, the component selected from the group consisting of (a) buffers, (b) monovalent ions; (c) divalent ions; (d) stabilizers; (e) proteins; (f) non-ionic detergents; (g) reducing agents; (h) compatible solutes; (i) sulfoxides; (j) amides; (k) tetraalkyl-ammonium salts; (l) polyhydroxyl alcohols; (m) chelating agents; (n) enzymes; (o) dNTPs; and (p) combinations thereof. and the like.

For example, a first reference data set is generated in a first defined reaction environment, and a second reference data set is generated in a second defined reaction environment; wherein the first defined reaction environment and the second defined reaction environment are different from each other. The difference between the first defined reaction environment and the second defined reaction environment indicates that the composition of the two reaction environments is different. For example, this may include the case where any one component is present in the first defined reaction environment but not in the second defined reaction environment as well as the case where the concentration of any one component in the first defined reaction environment is different from the concentration in the second defined reaction environment.

In other words, the defined reaction environment herein is different for each reference data set. As used herein, the expression "the defined reaction environment is different for each reference data set" means that the reaction environment in which the melting temperatures of reference oligonucleotides in a reference data set are experimentally measured is different from the reaction environment in which the melting temperatures of reference oligonucleotides in another reference data set are experimentally measured. As an example, a first reference data set may include the melting temperatures of reference oligonucleotides, experimentally measured in a reaction environment containing 1 M NaCl, while a second reference data set may include the melting temperatures of reference oligonucleotides, experimentally measured in a reaction environment containing 0.1 M NaCl. As another example, a first reference data set may include the melting temperatures of reference oligonucleotides, experimentally measured in a first reaction environment, while a second reference data set may include the melting temperatures of reference oligonucleotides, experimentally measured in a second reaction environment further comprising an additional component.

The number of differently defined reaction environments corresponds to the number of reference data sets. For example, when there are three differently defined reaction environments, the corresponding reference data sets, i.e., three reference data sets are The differently defined reaction environment means at least two different reaction environments. In one embodiment, the differently defined reaction environments comprise 2, 3, 4, 5, 6, 7, 8, 9, 10, or more reaction environments.

As used herein, the term "experimental melting temperature ($T_m$)" of a reference oligonucleotide refers to a $T_m$ of a reference oligonucleotide which is determined experimentally in a defined reaction environment. The experimental $T_m$ may be determined by melting curve analysis known in the art. As an example, the experimental $T_m$ of a reference oligonucleotide may be determined by measuring the change in absorbance from the duplex between the oligonucleotide and its complement as a function of temperature. As another example, the experimental $T_m$ of a reference oligonucleotide may be determined by measuring the change in fluorescence signal from the duplex between the oligonucleotide and its complement (e.g., by using an intercalating dye) as a function of temperature.

It is well known in the art that the $T_m$ of an oligonucleotide vary depending on the reaction environment in which the oligonucleotide is used/placed/applied. For the purpose of accurately predicting the $T_m$ of an oligonucleotide of interest in a desired reaction environment, the method of the present invention employs the experimental $T_m$s of reference oligonucleotides when placed in the same reaction environment as the oligonucleotide of interest.

Thus, reference oligonucleotides for providing their sequences and $T_m$s included in a reference data set may be selected from oligonucleotides having experimental $T_m$s measured in the same reaction environment as the reaction environment in which an oligonucleotide of interest to be placed, or may be prepared by experimentally measuring the $T_m$s of the reference oligonucleotides in the same reaction environment as the reaction environment in which an oligonucleotide of interest to be placed. For example, if it is desired to predict the $T_m$ of an oligonucleotide of interest in a first reaction environment, reference oligonucleotides may be selected from oligonucleotides having experimental $T_m$s measured in the first reaction environment, or may be prepared by selecting (synthesizing) any oligonucleotides and then experimentally measuring the $T_m$s of the oligonucleotides in the first reaction environment.

In one embodiment, each of the plurality of reference data sets comprises a plurality of reference oligonucleotides such that each NN sequence occurs with the frequency of at least two.

As used herein, the term "nearest-neighbor (NN) sequence" refers to a sequence consisting of two adjacent nucleotides (dinucleotide) in an oligonucleotide. The term may be used interchangeably with "nearest-neighbors", "nearest-neighbor base-pairs", or "nearest-neighbor pairs".

For example, in the case of an oligonucleotide sequence consisting of 13 bases of 5'-ATTGCTTGCTTCG-3', the total number of nearest-neighbor (NN) sequences is seven (7), i.e., "AT", "TT", "TG", "GC", "CT", "TC" and "CG". In this case, it is noted that "TT" occurs with the frequency of 3, "TG" with the frequency of 2, "GC" with the frequency of 2, "CT" with the frequency of 2.

The nearest-neighbor (NN) sequences possible are sixteen (16) types (4 bases×4 bases=16), e.g., "AA", "AT", "AG", "AC", "TA", "TT", "TG", "TC", "GA", "GT", "GG", "GC", "CA", "CT", "CG" and "CC". However, it is known that the dinucleotides "AA", "CA", "GT", "CT", "GA" and "GG" have the same NN parameter values as "TT", "TG", "AC", "AG", "TC" and "CC", respectively. Thus, the total number of nearest-neighbor (NN) sequences having parameter values to be determined is ten (10).

For the reference data set, the frequency for each of the NN sequences refers to the number of NN sequences occurred in reference oligonucleotides of the reference data set. That is, the frequency for each of the NN sequences in each reference data set can be obtained by calculating the sum of the number of each NN sequence from entire reference oligonucleotides. For example, if the reference data set has two reference oligonucleotides such as 5'-ATGT-3' and 5'-GTTA-3, the reference data set is said to have the frequency of 1 for AT, 1 for GT, 2 for GT, 1 for TT, and 1 for TA.

In one embodiment, each of the plurality of reference data sets comprises reference oligonucleotides such that such that each NN sequence occurs with the frequency of at least 2, at least 3, at least 4, at least 5, at least 7, at least 10, at least 15, at least 20, at least 30, or at least 40.

In one embodiment, each reference data set comprises a plurality of reference oligonucleotides such that the reference oligonucleotides have $T_m$s within a certain temperature range. For example, each reference data set comprises a plurality of reference oligonucleotides such that the reference oligonucleotides have $T_m$s between 30-100° C., 40-100° C., 50-100° C., 60-100° C., 30-90° C., 40-90° C., 50-90° C., 60-90° C., 30-80° C., 40-80° C., or 50-80° C.

In one embodiment, each reference data set comprises a plurality of reference oligonucleotides such that the reference oligonucleotides have $T_m$s with uniform distribution.

In one embodiment, each reference data set comprises at least one reference oligonucleotide having a $T_m$ falling within each temperature interval within a temperature range. The lower limit of the temperature range may be 20, 25, 30, 35, 40, 45, 50, 55, 60, 65, 70° C., or more. The upper limit of the temperature range may be 40, 45, 50, 55, 60, 65, 70, 75, 80, 85, 90, 95, 100° C., or more. The each temperature interval within a temperature range may have an interval of 3, 5, 7, 10, 15, 20, 25, 30, 35 or 40° C. As an example, when each temperature interval has an interval of 5° C., 10° C., 15° C. or therebetween, each reference data set may comprise at least one reference oligonucleotide having a $T_m$ falling within the each temperature interval. Specifically, when the temperature range consists of temperature intervals of 30-40° C., 40-50° C., 50-60° C., 60-70° C., and 70-80° C., each reference data set may comprise at least one reference oligonucleotide having an experimental $T_m$ of 30-40° C., at least one reference oligonucleotide having an experimental $T_m$ of 40-50° C., at least one reference oligonucleotide having an experimental $T_m$ of 50-60° C., at least one reference oligonucleotide having an experimental $T_m$ of 60-70° C., and at least one reference oligonucleotide having an experimental $T_m$ of 70-80° C.

Step (b): Establishment of an Equation for $T_m$ Calculation

Afterwards, an equation for $T_m$ calculation for each of the differently defined reaction environments is established using each of the plurality of reference data sets including the information (i)-(ii); wherein the establishment of the equation comprises determining the values of the parameters in the equation, wherein the parameters comprise nearest-neighbor (NN) thermodynamic parameters; and In this step, each of the plurality of reference data sets is used to establish an equation for $T_m$ calculation for each reference data set, i.e., for differently defined reaction environments, by determining the values of the parameters included in the equation.

An equation for $T_m$ calculation for each of the differently defined reaction environments will be described in detail below.

Equation for $T_m$ Calculation

The defined equation for $T_m$ calculation refers to any equation based on an NN model using thermodynamic parameters. The equation may be one known in the art or a modification thereof. The predicted $T_m$ of the oligonucleotide may be varied according to the equation used.

The equation for $T_m$ calculation used in the present invention is one comprising nearest-neighbor (NN) thermodynamic parameters, or a modification thereof.

In an embodiment, the equation for $T_m$ calculation comprises the enthalpy change ($\Delta H$) and the entropy change ($\Delta S$) for each of nearest-neighbor (NN) sequences.

In a particular embodiment, the equation for $T_m$ calculation is represented by the following Equation I.

$$Tm = \frac{\Delta H° \times m}{\Delta S°} - n \qquad \text{Equation I}$$

wherein $T_m$ is the melting temperature of the oligonucleotide; $\Delta H°$ is the sum of the enthalpy changes; $\Delta S°$ is the sum of the entropy changes; m and n are constants.

In the above equation, $\Delta H°$ can be calculated by the sum of each NN parameter $\Delta H°_{NN}$, and $\Delta S°$ can be calculated by the sum of each NN parameter $\Delta S°_{NN}$, as shown in the following Equation II.

$$\Delta H° = \Sigma_{NN} \text{ (each } \Delta H°_{NN}\text{)}, \Delta S° = \Sigma_{NN} \text{ (each } \Delta S°_N\text{)} \qquad \text{Equation II}$$

In the Equation I, m may be 1000 and n may be 273.15, but the m and n may be adjusted by the user. The equation for $T_m$ calculation can be found in SantaLucia, J. Jr (2007) Physical principles and visual-OMP software for optimal PCR design. Methods Mol. Biol., 402, 3-34.

In one specific embodiment, Equation I can also be expressed as Equation I-1.

$$Tm = \frac{\Delta H° \times 1000}{\Delta S°} - 273.15 \qquad \text{Equation I-1}$$

In an embodiment, the equation for $T_m$ calculation comprises the parameters of the enthalpy change ($\Delta H$) and the entropy change ($\Delta S$) for each of nearest-neighbor (NN) sequences, and one or more additional parameters.

In an embodiment, the one or more additional parameters comprise a parameter for correction (or supplement, amendment) of entropy change and/or a parameter for correction (or supplement, amendment) of $T_m$ contribution by length of the oligonucleotide.

In a particular embodiment, the equation for $T_m$ calculation is represented by the following Equation III.

$$Tm = \frac{\Delta H° \times m}{\Delta S° + \alpha} - n \qquad \text{Equation III}$$

wherein $T_m$ is the melting temperature of the oligonucleotide; $\Delta H°$ is the sum of the enthalpy changes; $\Delta S°$ is the sum of the entropy changes; $\alpha$ is a first additional parameter for correction of entropy change; and m and n are constants.

In this equation, the first additional parameter $\alpha$ for correction of entropy change is one determined additionally in step (b) besides the thermodynamic parameters ($\Delta H$® and $\Delta S°$). The first additional parameter may be referred to as "first correction parameter" or "parameter associated with entropy change". The value of the first additional parameter depends on the reaction environment.

In the above equation, $\Delta H°$ and $\Delta S°$ can be calculated as described above.

In one embodiment, m is 1000 and n is 273.15. The m and n may be adjusted by the user.

In one specific embodiment, Equation III can also be expressed in Equation III-1.

$$Tm = \frac{\Delta H° \times 1000}{\Delta S° + \alpha} - 273.15 \qquad \text{Equation III-1}$$

In another embodiment, the equation for $T_m$ calculation may be represented by the following Equation IV.

$$Tm = \frac{\Delta H° \times m}{\Delta S°} + \beta \ln(\text{length}) - n \qquad \text{Equation IV}$$

wherein $T_m$ is the melting temperature of the oligonucleotide; $\Delta H°$ is the sum of the enthalpy changes; $\Delta S°$ is the sum of the entropy changes; $\beta$ is a second additional parameter for correction of $T_m$ contribution by length of the oligonucleotide; length is the length of the oligonucleotide; m and n are constants.

In this equation, the second additional parameter $\beta$ is one determined additionally in step (b) besides the thermodynamic parameters ($\Delta H°$ and $\Delta S°$). The second additional parameter may be referred to as "second correction parameter"; "parameter associated with the length of the oligonucleotide sequence", or "parameter for the relationship between the length and $T_m$ of the oligonucleotide sequence". The second additional parameter $\beta$ is one for reflecting the influence of the reaction environment on the length of the oligonucleotide. The value of the second additional parameter depends on the reaction environment.

In the above equation, $\Delta H°$ and $\Delta S°$ can be calculated as described above.

In one embodiment, m is 1000 and n is 273.15. The m and n may be adjusted by the user.

In one specific implementation, Equation IV can also be expressed by Equation IV-1.

$$Tm = \frac{\Delta H° \times 1000}{\Delta S°} + \beta \ln(\text{length}) - 273.15 \qquad \text{Equation IV-1}$$

In another embodiment, the equation for calculation $T_m$ may be represented by the following Equation V.

$$Tm = \frac{\Delta H° \times m}{\Delta S° + \alpha} + \beta \ln(\text{length}) - n \qquad \text{Equation V}$$

wherein $T_m$ is the melting temperature of the oligonucleotide; $\Delta H°$ is the sum of the enthalpy changes; $\Delta S°$ is the sum of the entropy changes; a is a first additional parameter for correction of entropy change; $\beta$ is a second additional parameter for correction of $T_m$ contribution by length of the oligonucleotide; length is the length of the oligonucleotide; and m and n are constants.

In this equation, the first additional parameter and the second additional parameter are those determined additionally in step (b) besides the thermodynamic parameters ($\Delta H°$ and $\Delta S°$).

In the above equation, $\Delta H°$, $\Delta S°$, $\alpha$, and $\beta$ can be calculated as described above.

In one embodiment, m is 1000 and n is 273.15. The m and n may be adjusted by the user.

In one specific embodiment, Equation V can also be expressed as Equation V-1.

$$Tm_{(\alpha,\beta)} = \frac{\Delta H° \times 1000}{\Delta S° + \alpha} + \beta \ln(\text{length}) - 273.15 \qquad \text{Equation V-1}$$

In this equation, the first additional parameter and the second additional parameter are those determined additionally in step (b) besides the thermodynamic parameters ($\Delta H°$ and $\Delta S°$).

The equation for $T_m$ calculation may be selected by one of skill in the art, and it should be understood that various equations other than the above described equation can be used.

The establishment of the equation comprises determining the values of the parameters in the equation. The establishment of an equation for $T_m$ calculation, i.e., determination of the values of the parameters in the equation for $T_m$ calculation, is accomplished using each of the plurality of reference data sets including the information (i)-(ii).

The values of the parameters determined in this step will depend on the equation for $T_m$ calculation used in step (b).

In one embodiment, the values of the parameters determined in step (b) comprises the value of the enthalpy change ($\Delta H$) and the value of the entropy change ($\Delta S$) for each of ten (10) nearest-neighbor (NN) sequences.

In another embodiment, the values of the parameters determined in step (b) comprises the value of the enthalpy change ($\Delta H$) and the value of the entropy change ($\Delta S$) for each of ten (10) nearest-neighbor (NN) sequences, e.g., "AA", "AT", "TA", "GA", "GT", "GG", "GC", "CA", "CT", "CG", and one or more additional parameters. The one or more additional parameters may comprise a parameter for correction of entropy change and/or a parameter for correction of $T_m$ contribution by length of the oligonucleotide.

For example, where Equation I (in particular, Equation I-1) is used in the step (b) to calculate $T_m$, the values of the parameters determined in this step comprise the value of the enthalpy change ($\Delta H$) and the value of the entropy change ($\Delta S$) for each of ten (10) nearest-neighbor (NN) sequences, e.g., "AA", "AT", "TA", "GA", "GT", "GG", "GC", "CA", "CT", "CG". Since Equation I requires two NN parameters $\Delta H$ and $\Delta S$ for the $T_m$ calculation, the values of the two parameters in Equation I should be determined in this step (b). It is reported that the number of all possible NN sequences is a total of 16 (4 bases×4 bases), but 6 NN sequences of them have the same parameter values. Thus, the values of the parameters to be determined in this step (b) are for the 10 NN sequences.

Where Equation III (in particular, Equation III-1) is used in the step (b) to calculate $T_m$, the values of the parameters determined in this step comprise the value of the enthalpy change ($\Delta H$) and the value of the entropy change ($\Delta S$) for each of ten (10) nearest-neighbor (NN) sequences, e.g., "AA", "AT", "TA", "GA", "GT", "GG", "GC", "CA", "CT", "CG", and the first additional parameter (a parameter for correction of entropy change). Since Equation III requires one additional parameter besides the two NN parameters $\Delta H$ and $\Delta S$ for the $T_m$ calculation, a total of three parameters in Equation III should be determined in this step (b).

Where Equation IV (in particular, Equation IV-1) is used in the step (b) to calculate $T_m$, the values of the parameters determined in this step comprise the value of the enthalpy change ($\Delta H$) and the value of the entropy change ($\Delta S$) for each of ten (10) nearest-neighbor (NN) sequences, e.g., "AA", "AT", "TA", "GA", "GT", "GG", "GC", "CA", "CT", "CG", and the second additional parameter (a parameter for correction of $T_m$ contribution by length of the oligonucleotide). Since Equation IV requires one additional parameter besides the two NN parameters $\Delta H$ and $\Delta S$ for the $T_m$ calculation, a total of three parameters in Equation IV should be determined in this step (b).

Where Equation V (in particular, Equation V-1) is used in the step (b) to calculate $T_m$, the values of the parameters determined in this step comprise the value of the enthalpy change ($\Delta H$) and the value of the entropy change ($\Delta S$) for each of ten (10) nearest-neighbor (NN) sequences, e.g., "AA", "AT", "TA", "GA", "GT", "GG", "GC", "CA", "CT", "CG", and the first additional parameter (a parameter for correction of entropy change) and the second additional parameter (a parameter for correction of $T_m$ contribution by length of the oligonucleotide). Since Equation V requires two additional parameters besides the two NN parameters $\Delta H$ and $\Delta S$ for the $T_m$ calculation, a total of four parameters in Equation V should be determined in this step (b).

The determination of the values of the parameters in step (b) may be performed by linear regression or nonlinear regression. The determination of the values of the parameters means solving for 10 unknown In one embodiment, the determination of the values of the parameters in step (b) is performed by least square method. In an embodiment, the values of the parameters included in the equation are each determined for each NN sequence, by finding a value to minimize the sum of squared errors by least squares method The results of the determination of the values of the parameters in step (b) comprise the data of the thermodynamic parameters (in the case of Equations III, IV and V, further comprising one or more correction parameters), i.e., a table of thermodynamic parameters.

To date, a variety of NN tables have been published (Breslauer et al. (1986) Proc Natl Acad Sci USA 83: 3746-3750; Sugimoto et al. (1996), Nuc Acids Res 24: 4501-4505; Allawi and Santa Lucia Biochemistry 36: 10581-10594; SantaLucia & Hicks (2004), Annu. Rev. Biophys. Biomol. Struct 33: 415-440). However, the conventional NN tables propose the values of the NN parameters optimized for a fixed reaction environment, so that they are not suitable for use in calculating the $T_m$ of oligonucleotides in various reaction environments.

In contrast, the present invention is well suited for calculating the $T_m$ of an oligonucleotide in a variety of reaction environments using the values of the NN parameters optimized for each reaction environment.

As described above, Equation III, IV or V further comprises a first additional parameter for correcting the entropy change and/or a second additional parameter for correcting the oligonucleotide length, in addition to the NN parameters.

Some conventional equations have been developed, including a correction factor that reflects the salt concentration in the reaction environment or the length of an oligonucleotide. However, since the $T_m$ of an oligonucleotide is also affected by many other factors as well as it is difficult to establish the equation for $T_m$ calculation considering all of these correction factors, the approach using a correction factor is also not suitable for predicting an accurate $T_m$ of an oligonucleotide that reflects the entire reaction environment.

Further, the above method assumes that the values of the NN parameters for each NN sequence (also referred to as NN propagation) do not change for all reaction environments, except for the value of the correction factor. However, since such changes in the reaction environment also affect the values of the thermodynamic NN parameters for each NN sequence, the above approach has limitations in accurately predicting the $T_m$ of the oligonucleotide in various reaction environments.

In contrast, according to the method of the present invention, the values of the additional parameters used in Equation III, IV or V as well as the values of the NN parameters vary depending on reaction environment. That is, the method of the present invention is distinct from the conventional methods, in terms of the variability in the values of the NN parameters and the value(s) of the additional parameter(s) depending on the reaction environment. The method of the present invention can accurately predict the change of $T_m$ depending on varying reaction environment by using various parameters depending on the change in the reaction environment.

In one embodiment, the equation for $T_m$ calculation used to determine the values of the parameters is the same for all reaction environments. For example, the equation for $T_m$ calculation used in a first reference data set may be Equation V and the equation for $T_m$ calculation used in a second reference data set may also be Equation V.

In another embodiment, the equation for $T_m$ calculation used to determine the values of the parameters is different for some reaction environments. For example, the equation for $T_m$ calculation used in a first reference data set may be Equation I, while the equation for $T_m$ calculation used in a second reference data set may be Equation V.

In one embodiment, the values of the parameters determined are different for all reaction environments. For example, the value of the enthalpy change (ΔH) and the value of the entropy change (ΔS) for each of ten nearest-neighbor (NN) sequences and the value of the first additional parameter and the value of the second additional parameter determined for a first reference data set are different from those determined for a second reference data set. The difference in these parameter values for different reaction environments ultimately leads to the difference in the predicted $T_m$ of an oligonucleotides of interest in different reaction environments.

Step (c): Calculating the $T_m$ of an Oligonucleotide of Interest in a Defined Reaction Environment In this step, the $T_m$ of an oligonucleotide of interest in one among the differently defined reaction environments is calculated using the equation established for the one among the differently defined reaction environments The established equations for $T_m$ calculations for the differently defined reaction environments can be used to predict the $T_m$ of an oligonucleotide of interest in various reaction environments.

Specifically, the equations having the parameter values determined for the differently defined reaction environments are provided in step (c).

In one embodiment, the values of the parameters comprise the value of the enthalpy change (ΔH) and the value of the entropy change (ΔS) for each of the ten nearest-neighbor (NN) sequences. In another embodiment, the values of the parameters comprise the value of the enthalpy change (ΔH) and the value of the entropy change (ΔS) for each of the nearest-neighbor (NN) sequence and the value of one or more additional parameters, wherein the one or more additional parameters comprise a parameter for correction of entropy change and/or a parameter for correction of length of the oligonucleotide.

In this step, the $T_m$ of an oligonucleotide of interest in one among the differently defined reaction environments is calculated using the equation established for the one among the differently defined reaction environments The melting temperature of the oligonucleotide of interest calculated in this step is referred to herein as the "predicted $T_m$", as it is determined by the equation established by the method of the present invention, rather than determined by any experimentation including melting analysis, For example, the predicted $T_m$ of an oligonucleotide of interest in a first reaction environment may be calculated by the equation for $T_m$ calculation having the parameter values determined using a first reference data set (comprising information about the sequences of a plurality of reference oligonucleotides and information about the experimental $T_m$s of the plurality of reference oligonucleotides in the first reaction environment); whereas the predicted $T_m$ of an oligonucleotide of interest in a second reaction environment may be calculated by the equation for $T_m$ calculation having the parameter values determined using a second reference data set (comprising information about the sequences of a plurality of reference oligonucleotides and information about the experimental $T_m$s of the plurality of reference oligonucleotides in the second reaction environment).

The established equation for each of the differently defined reaction environments is used to calculate the melting temperature of an oligonucleotide of interest in the each of the differently defined reaction environments.

In one embodiment, where Equation I having the parameter values determined for a particular reference data set is established in step (b), the melting temperature of an oligonucleotide of interest is calculated as follows:

First, the N−1 NN sequences of an oligonucleotide of interest consisting of N nucleotides are provided. Thereafter, the values of the NN parameters for the N−1 NN sequences of an oligonucleotide of interest as determined in step (b) is applied to the above established Equation I to calculate the $T_m$ of an oligonucleotide of interest.

In one embodiment, where Equation III, IV or V having the parameter values determined for a particular reference data set is established in step (b), the melting temperature of an oligonucleotide of interest is calculated as follows:

First, the N−1 NN sequences of an oligonucleotide of interest consisting of N nucleotides and the length N of the oligonucleotide (for Equations IV and V only) are provided. Thereafter, the values of the NN parameters for the N−1 NN sequences of an oligonucleotide of interest, and the value of the first additional parameter and/or the value of the second additional parameter, and the length N of the oligonucleotide (for Equations IV and V only) as determined in step (b) are applied to each established equation to calculate the $T_m$ of an oligonucleotide of interest.

According to the method of the present invention, it is possible to accurately calculate the melting temperature of an oligonucleotide when used in various reaction environments. That is, the method of the present invention can accurately calculate not only the melting temperature of an oligonucleotide when present in a first reaction environment but also the melting temperature of the oligonucleotide when present in a second reaction environment.

According to the method of the present invention, the parameter values determined in a first reaction environment may be different from those in a second reaction environment, and thus the predicted $T_m$ of the oligonucleotide in the first reaction environment may be different from that in the second reaction environment.

According to the method of the present invention, it is possible to establish various equations having the parameter values optimized for various reaction environments and to predict the $T_m$ of an oligonucleotide of interest in a particular reaction environment by using a corresponding established equation. If there is no equation available for a particular reaction environment, the $T_m$ of an oligonucleotide of interest can be predicted using an equation having the parameter values as determined in a similar reaction environment, or with slight modification of the predicted $T_m$.

II. Method for Predicting the Melting Temperature ($T_m$) of an Oligonucleotide in a Defined Reaction Environment In a second aspect of this invention, there is a method for predicting the melting temperature ($T_m$) of an oligonucleotide of interest in a defined environment, comprising the steps of:
  (a) providing a reference data set, wherein the reference data set comprises (i) information about the sequences of a plurality of reference oligonucleotides and (ii) information about the experimental $T_m$s of the plurality of reference oligonucleotides in a defined reaction environment;
  (b) establishing an equation for $T_m$ calculation for the defined reaction environment using the reference data set including the information (i)-(ii); wherein the establishment of the equation comprises determining the values of the parameters in the equation, wherein the parameters comprise nearest-neighbor (NN) thermodynamic parameters; and
  (c) calculating the $T_m$ of an oligonucleotide of interest in the defined reaction environment using the established equation for $T_m$ calculation.

The second aspect of the present invention will now be described in detail.

Step (a): Providing a Reference Data Set 110

First, a reference data set is provided 110. The reference data set comprises (i) information about the sequences of a plurality of reference oligonucleotides and (ii) information about the experimental $T_m$s of the plurality of reference oligonucleotides in a defined reaction environment.

Details of the reference data set can be found in the section of the first aspect of the present invention.

According to this aspect, the method of the present invention uses a single reference data set, in order to predict the melting temperature of an oligonucleotide of interest in a defined reaction environment; wherein the reference data set corresponds to the defined reaction environment.

The reference data set is used herein to establish an NN model optimized for a defined reaction environment and to calculate the $T_m$ of an oligonucleotide of interest in the defined reaction environment.

The reference data set comprises (i) information about the sequences of a plurality of reference oligonucleotides and (ii) information about the experimental $T_m$s of the plurality of reference oligonucleotides in a defined reaction environment.

The components constituting the reference data set will be described in detail.

(i) Information about the Sequences of a Plurality of Reference Oligonucleotides The reference data set includes information about the sequences of a plurality of reference oligonucleotides. The information about the sequences of a plurality of reference oligonucleotides comprises information about nearest-neighbor (NN) sequences derived from a plurality of reference oligonucleotides The number of the sequences of the reference oligonucleotides included in the reference data set is not particularly limited, as long as all the values of the thermodynamic parameters for the nearest-neighbor (NN) sequences (also referred to as NN propagation, preferably a total of 10 NN sequences) can be determined using the sequences of the reference oligonucleotides. The number of the sequences of the reference oligonucleotides included in the reference data set is preferably as large as possible for accurate determination of the NN parameter values, but it may be adjusted to reduce the time required for determination of the NN parameter values, and the like. For example, the number of the sequences of the reference oligonucleotides in the reference data set may be at least 20, at least 30, or at least 50, up to 100, up to 300, up to 500, up to 1000, up to 3000, or 5000.

(ii) Information about the Experimental $T_m$s of the Plurality of Reference Oligonucleotides in a Defined Reaction Environment The reference data set includes information about the experimental $T_m$s of the plurality of reference oligonucleotides in a defined reaction environment.

As used herein, the term "experimental melting temperatures of a plurality of reference oligonucleotides in a defined reaction environment" refers to an experimental measure of melting temperature of each of the reference oligonucleotides in a defined reaction environment.

As used herein, the term "reaction environment" refers to one in which the oligonucleotide whose $T_m$ is to be predicted (oligonucleotide of interest) is used/placed/applied. In other words, the term "reaction environment" refers to the medium, particularly chemical characteristics, surrounding an oligonucleotide. The reaction environment may be defined by the types and concentrations of the components used in a reaction except the oligonucleotide of interest. For example, when an oligonucleotide whose $T_m$ is to be predicted is used in a PCR reaction, examples of the components can be used in the reaction include, without limitation, a buffers (for pH adjustment) such as Tris, Tricine, bis Tricine, HEPES, EPPS, CHES and CAPSO; monovalent ions such as KCl, $(NH_4)_2SO_4$, NaCl, LiCl, $NH_4Cl$, $NaN_3$, $CoCl_2$, KOAc, KSO4, $(Mn(OAc))_2$ and NaOAc; divalent ions such as $MgCl_2$, $MgSO_4$, $MgSO_4$, and $ZnCl_2$; stabilizers such as BSA and gelatin; proteins such as T4 gene 32 protein and Et SSB; non-ionic detergents such as NP-40, Tween20, Triton X-100, Triton X-114, CHAPSO, IGEPAL, CHAPS, MEGA-8, Brij 35 and BRIJ 58; reducing agents such as DTT, b-mercaptoethanol and TCEP; compatible solutes such as glycerol, trehalose, sucrose, xylitol, melezitose, xylene cyanol, mannose, sorbitol, mannitol, betaine, ectoine and proline; sulfoxides such as DMSO; amides such as formamide; tetraalkyl-ammonium salts such as TMAC and TMAA, Polyhydroxyl alcohols such as propylene glycol and polyvinyl alcohol (PVA); chelating agent such as EDTA and EGTA; enzymes such as polymerases, dNTPs, and the like.

In one embodiment, the reaction environment may exclude a reaction environment comprising 1 M NaCl.

As used herein, the term "experimental melting temperature ($T_m$)" of a reference oligonucleotide refers to a $T_m$ of a reference oligonucleotide which is determined experimentally in a defined reaction environment. The experimental $T_m$ may be determined by melting curve analysis known in the art. As an example, the experimental $T_m$ of a reference oligonucleotide may be determined by measuring the change in absorbance from the duplex between the oligonucleotide and its complement as a function of temperature. As another example, the experimental $T_m$ of a reference oligonucleotide may be determined by measuring the change in fluorescence signal from the duplex between the oligonucleotide and its complement (e.g., by using an intercalating dye) as a function of temperature.

It is well known in the art that the $T_m$ of an oligonucleotide vary depending on the reaction environment in which the oligonucleotide is used/placed/applied. For the purpose of accurately predicting the $T_m$ of an oligonucleotide of interest in a desired reaction environment, the method of the present invention employs the experimental $T_m$s of reference oligonucleotides when placed in the same reaction environment as the oligonucleotide of interest.

Thus, reference oligonucleotides for providing their sequences and $T_m$s included in a reference data set may be selected from oligonucleotides having experimental $T_m$s measured in the same reaction environment as the reaction environment in which an oligonucleotide of interest to be placed, or may be prepared by experimentally measuring the $T_m$s of the reference oligonucleotides in the same reaction environment as the reaction environment in which an oligonucleotide of interest to be placed.

In one embodiment, the reference data set comprises a plurality of reference oligonucleotides such that each NN sequence occurs with the frequency of at least two.

As used herein, the term "nearest-neighbor (NN) sequence" refers to a sequence consisting of two adjacent nucleotides (dinucleotide) in an oligonucleotide. The term may be used interchangeably with "nearest-neighbors", "nearest-neighbor base-pairs", or "nearest-neighbor pairs".

For example, in the case of an oligonucleotide sequence consisting of 13 bases of 5'-ATTGCTTGCTTCG-3', the total number of nearest-neighbor (NN) sequences is seven (7), i.e., "AT", "TT", "TG", "GC", "CT", "TC" and "CG". In this case, it is noted that "TT" occurs with the frequency of 3, "TG" with the frequency of 2, "GC" with the frequency of 2, "CT" with the frequency of 2.

The nearest-neighbor (NN) sequences possible are sixteen (16) types (4 bases×4 bases=16), e.g., "AA", "AT", "AG", "AC", "TA", "TT", "TG", "TC", "GA", "GT", "GG", "GC", "CA", "CT", "CG" and "CC". However, it is known that the dinucleotides "AA", "CA", "GT", "CT", "GA" and "GG" have the same NN parameter values as "TT", "TG", "AC", "AG", "TC" and "CC", respectively. Thus, the total number of nearest-neighbor (NN) sequences having parameter values to be determined is ten (10).

For the reference data set, the frequency for each of the NN sequences refers to the number of NN sequences occurred in reference oligonucleotides of the reference data set. That is, the frequency for each of the NN sequences in the reference data set can be obtained by calculating the sum of the number of each NN sequence from entire reference oligonucleotides. For example, if the reference data set has two reference oligonucleotides such as 5'-ATGT-3' and 5'-GTTA-3', the reference data set is said to have the frequency of 1 for AT, 1 for GT, 2 for GT, 1 for TT, and 1 for TA.

In one embodiment, the reference data set comprises reference oligonucleotides such that such that each NN sequence occurs with the frequency of at least 2, at least 3, at least 4, at least 5, at least 7, at least 10, at least 15, at least 20, at least 30, or at least 40.

In one embodiment, the reference data set comprises at least one reference oligonucleotide having a $T_m$ falling within each temperature interval within a temperature range.

The lower limit of the temperature range may be 20, 25, 30, 35, 40, 45, 50, 55, 60, 65, 70° C., or more. The upper limit of the temperature range may be 40, 45, 50, 55, 60, 65, 70, 75, 80, 85, 90, 95, 100° C., or more. The each temperature interval within a temperature range may have an interval of 3, 5, 7, 10, 15, 20, 25, 30, 35 or 40° C. As an example, when each temperature interval has an interval of 5° C., 10° C., 15° C. or therebetween, the reference data set may comprise at least one reference oligonucleotide having a $T_m$ falling within the each temperature interval. Specifically, when the temperature range consists of temperature intervals of 30-40° C., 40-50° C., 50-60° C., 60-70° C., and 70-80° C., the reference data set may comprise at least one reference oligonucleotide having an experimental $T_m$ of 30-40° C., at least one reference oligonucleotide having an experimental $T_m$ of 40-50° C., at least one reference oligonucleotide having an experimental $T_m$ of 50-60° C., at least one reference oligonucleotide having an experimental $T_m$ of 60-70° C., and at least one reference oligonucleotide having an experimental $T_m$ of 70-80° C.

Step (b): Establishment of a Defined Equation for Tm Calculation

Afterwards, an equation for $T_m$ calculation for the defined reaction environment is established using the reference data set including the information (i)-(ii); wherein the establishment of the equation comprises determining the values of the parameters in the equation, wherein the parameters comprise nearest-neighbor (NN) thermodynamic parameters; and In this step, the reference data set is used to establish an equation for $T_m$ calculation for the reference data set, i.e., for the defined reaction environments, by determining the values of the parameters included in the equation.

The defined equation for $T_m$ calculation refers to any equation based on an NN model using thermodynamic parameters. The equation may be one known in the art or a modification thereof. The predicted $T_m$ of the oligonucleotide may be varied according to the equation used.

The equation for $T_m$ calculation used in the present invention is one comprising nearest-neighbor (NN) thermodynamic parameters, or a modification thereof.

In an embodiment, the equation for $T_m$ calculation comprises the parameters of the enthalpy change (ΔH) and the entropy change (ΔS) for each of nearest-neighbor (NN) sequences, and one or more additional parameters.

In an embodiment, the one or more additional parameters comprise a parameter for correction (or supplement) of entropy change and/or a parameter for correction (or supplement) of length of the oligonucleotide.

In an embodiment, the equation for $T_m$ calculation is represented by the following Equation V.

$$Tm = \frac{\Delta H° \times m}{\Delta S° + \alpha} + \beta \ln(\text{length}) - n \qquad \text{Equation V}$$

wherein $T_m$ is the melting temperature of the oligonucleotide; ΔH° is the sum of the enthalpy changes; ΔS° is the sum of the entropy changes; α is a first additional parameter for correction of entropy change; β is a second additional parameter for correction of length of the oligonucleotide; length is the length of the oligonucleotide; and m and n are constants.

In this equation, the first additional parameter α for correction of entropy change is one determined additionally in step (b) besides the thermodynamic parameters (ΔH° and ΔS°). The first additional parameter may be referred to as "first correction parameter" or "parameter associated with entropy change". The value of the first additional parameter depends on the reaction environment.

In this equation, the second additional parameter β is one determined additionally in step (b) besides the thermodynamic parameters (ΔH° and ΔS°). The second additional parameter may be referred to as "second correction parameter"; "parameter associated with the length of the oligonucleotide sequence", or "parameter for the relationship between the length and $T_m$ of the oligonucleotide sequence". The second additional parameter β is one for reflecting the influence of the reaction environment on the length of the oligonucleotide. The value of the second additional parameter depends on the reaction environment.

In a particular embodiment, m is 1000 and n is 273.15.

Details of the reference oligonucleotide sequences, their experimental $T_m$s, and the defined equation for $T_m$ calculation can be found in the section of the first aspect of the present invention.

Step (c): Calculating the $T_m$ of an Oligonucleotide of Interest in the Defined Reaction Environment In this step, the $T_m$ of an oligonucleotide of interest in the defined reaction environment is calculated using the established equation for $T_m$ calculation The established equation for $T_m$ calculation having the parameter values determined for the defined reaction environment is provided in step (c). The established equation for $T_m$ calculation having the parameter values determined for the defined reaction environment can be used to predict the $T_m$ of an oligonucleotide of interest in the defined reaction environment.

In one embodiment, the values of the parameters comprise the value of the enthalpy change (ΔH) and the value of the entropy change (ΔS) for each of the ten nearest-neighbor (NN) sequences. In another embodiment, the values of the parameters comprise the value of the enthalpy change (ΔH) and the value of the entropy change (ΔS) for each of the nearest-neighbor (NN) sequence and the value of one or more additional parameters, wherein the one or more additional parameters comprise a parameter for correction of entropy change and/or a parameter for correction of length of the oligonucleotide.

The calculation of the melting temperature can be found in the section of the first aspect of the present invention.

According to the second aspect of the present invention, it is possible to accurately calculate the melting temperature of an oligonucleotide when placed in a specific reaction environment.

III. Storage Medium and Device for Predicting the Melting Temperature of an Oligonucleotide In another aspect of this invention, there is provided a computer readable storage medium containing instructions to configure a processor to a method for predicting the melting temperature ($T_m$) of an oligonucleotide, comprising:
 (a) receiving information about the sequence of an oligonucleotide of interest; and
 (b) applying the information to one of established equations for $T_m$ calculation, thereby calculating the $T_m$ of an oligonucleotide of interest in one among differently defined reaction environments;
 wherein the established equations for $T_m$ calculation are provided by the method, comprising:
 providing a plurality of reference data sets, wherein the reference data set comprises (i) information about the sequences of a plurality of reference oligonucleotides and (ii) information about the experimental $T_m$s of the plurality of reference oligonucleotides in a defined reaction environment, wherein the plurality of reference data sets are generated in differently defined reaction environments; and
 establishing an equation for $T_m$ calculation for each of the differently defined reaction environments using the information (i)-(ii) included in each of the plurality of reference data sets; wherein the establishment of the equation comprises determining the values of the parameters in the equation, wherein the parameters comprise nearest-neighbor (NN) thermodynamic parameters.

In a further aspect of this invention, there is provided a device for predicting the melting temperature of an oligonucleotide, comprising (a) a computer processor and (b) the computer readable storage medium described above coupled to the computer processor.

Since the storage medium and the device of the prevent invention described hereinbelow are intended to perform the present methods in a computer, the common descriptions between them are omitted in order to avoid undue redundancy leading to the complexity of this specification.

The program instructions are operative, when performed by the processor, to cause the processor to perform the present method described above. The program instructions for predicting the melting temperature of an oligonucleotide of interest may comprise (i) an instruction to receive sequence information about an oligonucleotide of interest; and (b) an instruction to apply the information to an established equation for $T_m$ calculation, thereby calculating the $T_m$ of an oligonucleotide of interest.

In the program instructions, the established equation for $T_m$ calculation is provided by the method of the first or second aspect of the present invention.

Further, the program instructions that perform the prediction of the $T_m$ of the oligonucleotide may further comprise instructions to display the predicted melting temperature of an oligonucleotide of interest to the display device.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

The processor may be prepared in such a manner that a single processor can do several performances. Alternatively, the processor unit may be prepared in such a manner that several processors do the several performances, respectively.

The features and advantages of this invention will be summarized as follows:

Conventional $T_m$ prediction methods predict the $T_m$ of an oligonucleotide in various reaction environments by using an equation having the NN parameter values optimized for a fixed reaction environment. However, the difference between the environment in which the NN parameter values are derived and the environment in which the oligonucleotide having the $T_m$ to be predicted is used may lead to an inaccurate prediction of $T_m$ of an oligonucleotide. In contrast, the method of the present invention can accurately predict the $T_m$ of an oligonucleotide in various reaction environments by the use of the parameter values optimized for the corresponding reaction environments, which is useful in the field of molecular biology involving hybridization, particularly in PCR.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Prediction of Melting Temperature of Oligonucleotide Using Nearest-Neighbor (NN) Parameters Optimized for Specific Reaction Environment A reference data set, comprising the sequences of a plurality of reference oligonucleotides and their experimental $T_m$s measured in a specific reaction environment, was used to determine the values of the nearest-neighbor (NN) thermodynamic parameters included in a $T_m$ prediction model. Then, the $T_m$ prediction model having the determined NN parameter values was used to calculate the predicted $T_m$ of an oligonucleotide of interest in the reaction environment. The predicted $T_m$ means a $T_m$ of an oligonucleotide expected to have in a specific reaction environment (particularly, the composition of a buffer containing an enzyme), which is calculated by a $T_m$ prediction model. The predicted $T_m$ may depend on the reaction environment in which an oligonucleotide is used.

In this Example, a known equation for $T_m$ calculation based on the NN model was used as a $T_m$ prediction model. The values of the parameters included in the equation were each determined for each NN sequence, by finding a value to minimize the sum of squared errors by least squares method. Then, the equation for $T_m$ calculation having the parameter values thus determined was used to calculate the predicted $T_m$ of an oligonucleotide of interest. Next, an error between the experimental $T_m$ and the prediction $T_m$ of an oligonucleotide of interest was calculated to evaluate the $T_m$ prediction performance of the above equation. The values of the parameters as determined above were compared with values of the parameters previously known in the art.

<1-1> Preparation of Oligonucleotides and Measurement of $T_m$

Ninety-five (95) oligonucleotides of varying sequences and lengths were prepared and their experimental $T_m$s were determined by melting curve analysis.

Specifically, a hybridizing oligonucleotide complementary to each oligonucleotide was prepared, and the formation of a duplex between each oligonucleotide and its complementary hybridizing oligonucleotide was detected using an intercalating dye. The experimental $T_m$ of each oligonucleotide was determined by melting the resulting duplex.

Briefly, the reaction was conducted in the final volume of 20 µl 0.05 uM of oligonucleotide for $T_m$ measurement, 0.05 uM of hybridizing oligonucleotide, 1× EvaGreen (Biotium, USA) as an intercalating dye, and 5 µl of 4× Master Mix (final, 200 uM dNTPs, 2 mM $MgCl_2$, 2 U of Taq DNA polymerase) (Enzynomics, Korea); the tube containing the reaction mixture was placed in the real-time thermocycler (CFX96, Bio-Rad); the reaction mixture was subjected to melting curve analysis consisting of 5 minutes at 50° C., 15 minutes at 95° C., 10 minutes at 50° C., and slow heating from 50° C. to 85° C. by 0.5° C. The fluorescence was measured continuously during the temperature rise and the experimental $T_m$s of the ninety-five (95) oligonucleotides were determined.

<1-2> Providing Reference Data Set

Thirty-seven (37) oligonucleotides (about 39%) out of the 95 oligonucleotides having the experimental $T_m$s were selected as reference oligonucleotides for calculation of NN parameters optimized for the reaction environment of this example. The reference oligonucleotides were selected such that each NN sequence occurs with the frequency of at least 20. The sequences and the melting temperatures of the reference oligonucleotides were pooled to prepare a reference data set.

For the reference data set, the length and experimental $T_m$ of each reference oligonucleotide and the frequency for each NN sequence are shown in Table 1 below.

TABLE 1

| | Ex. $T_m$ | length | AA/TT | AT/TA | AG/TC | AC/TG | TA/AT | TT/AA | TG/AC | TC/AG | GA/CT | GT/CA | GG/CC | GC/CG | CA/GT | CT/GA | CG/GC | CC/GG |
|---|---|---|---|---|---|---|---|---|---|---|---|---|---|---|---|---|---|---|
| oligo1 | 53.8 | 17 | 2 | 2 | 1 | 1 | 0 | 0 | 2 | 0 | 4 | 0 | 1 | 0 | 1 | 0 | 1 | 1 |
| oligo2 | 54.5 | 23 | 1 | 3 | 0 | 1 | 3 | 7 | 1 | 1 | 0 | 1 | 0 | 0 | 1 | 1 | 0 | 2 |
| oligo3 | 55.3 | 20 | 2 | 2 | 0 | 1 | 2 | 2 | 2 | 0 | 1 | 1 | 1 | 1 | 1 | 1 | 1 | 1 |
| oligo4 | 57.0 | 17 | 2 | 1 | 0 | 0 | 0 | 4 | 0 | 1 | 1 | 0 | 2 | 2 | 0 | 1 | 2 | 0 |
| oligo5 | 57.3 | 18 | 2 | 2 | 1 | 1 | 0 | 0 | 2 | 0 | 4 | 0 | 1 | 0 | 1 | 0 | 1 | 2 |
| oligo6 | 57.5 | 21 | 2 | 2 | 0 | 1 | 2 | 2 | 2 | 0 | 1 | 1 | 1 | 1 | 1 | 1 | 1 | 2 |
| oligo7 | 58.0 | 21 | 1 | 1 | 2 | 1 | 2 | 0 | 0 | 3 | 0 | 1 | 1 | 2 | 2 | 3 | 1 | 0 |
| oligo8 | 58.5 | 18 | 0 | 0 | 0 | 2 | 1 | 2 | 1 | 1 | 0 | 0 | 0 | 3 | 1 | 3 | 2 | 1 |
| oligo9 | 58.5 | 27 | 1 | 5 | 1 | 1 | 3 | 5 | 1 | 3 | 0 | 2 | 0 | 0 | 3 | 1 | 0 | 0 |
| oligo10 | 59.0 | 19 | 2 | 1 | 2 | 0 | 0 | 1 | 2 | 1 | 2 | 0 | 1 | 2 | 1 | 2 | 0 | 1 |
| oligo11 | 59.0 | 19 | 0 | 0 | 2 | 0 | 1 | 3 | 3 | 0 | 1 | 3 | 2 | 1 | 0 | 2 | 0 | 0 |
| oligo12 | 59.0 | 27 | 0 | 2 | 2 | 0 | 2 | 9 | 2 | 2 | 1 | 2 | 0 | 1 | 1 | 2 | 0 | 0 |
| oligo13 | 60.0 | 26 | 1 | 3 | 0 | 1 | 3 | 7 | 1 | 2 | 0 | 1 | 0 | 0 | 1 | 2 | 1 | 2 |
| oligo14 | 60.0 | 21 | 3 | 2 | 1 | 1 | 1 | 0 | 2 | 1 | 3 | 1 | 1 | 1 | 0 | 0 | 2 | 1 |
| oligo15 | 60.0 | 21 | 3 | 2 | 1 | 1 | 1 | 0 | 2 | 1 | 3 | 1 | 1 | 1 | 0 | 0 | 2 | 1 |

TABLE 1-continued

| | Ex. T$_m$ | length | AA/ TT | AT/ TA | AG/ TC | AC/ TG | TA/ AT | TT/ AA | TG/ AC | TC/ AG | GA/ CT | GT/ CA | GG/ CC | GC/ CG | CA/ GT | CT/ GA | CG/ GC | CC/ GG |
|---|---|---|---|---|---|---|---|---|---|---|---|---|---|---|---|---|---|---|
| oligo16 | 60.0 | 21 | 4 | 2 | 2 | 1 | 0 | 0 | 1 | 1 | 4 | 0 | 2 | 0 | 0 | 0 | 1 | 2 |
| oligo17 | 60.0 | 21 | 4 | 2 | 2 | 1 | 0 | 0 | 1 | 1 | 4 | 0 | 2 | 0 | 0 | 0 | 1 | 2 |
| oligo18 | 60.0 | 20 | 0 | 2 | 2 | 1 | 0 | 3 | 0 | 3 | 2 | 0 | 2 | 0 | 2 | 1 | 1 | 0 |
| oligo19 | 60.3 | 22 | 2 | 2 | 0 | 1 | 2 | 2 | 2 | 1 | 1 | 1 | 1 | 1 | 1 | 1 | 1 | 2 |
| oligo20 | 61.0 | 20 | 0 | 0 | 1 | 2 | 0 | 5 | 1 | 1 | 2 | 2 | 1 | 0 | 1 | 1 | 2 | 0 |
| oligo21 | 61.0 | 22 | 5 | 2 | 2 | 1 | 0 | 0 | 2 | 1 | 2 | 0 | 1 | 1 | 2 | 1 | 0 | 1 |
| oligo22 | 61.8 | 22 | 5 | 2 | 1 | 2 | 0 | 0 | 2 | 0 | 4 | 0 | 1 | 0 | 1 | 0 | 1 | 2 |
| oligo23 | 62.0 | 23 | 2 | 0 | 2 | 1 | 2 | 3 | 3 | 0 | 1 | 3 | 2 | 1 | 0 | 2 | 0 | 0 |
| oligo24 | 62.5 | 20 | 0 | 0 | 0 | 3 | 2 | 2 | 1 | 1 | 0 | 0 | 0 | 3 | 1 | 3 | 2 | 1 |
| oligo25 | 62.5 | 20 | 0 | 0 | 2 | 0 | 1 | 2 | 4 | 0 | 2 | 3 | 2 | 1 | 0 | 2 | 0 | 0 |
| oligo26 | 63.0 | 25 | 4 | 3 | 2 | 1 | 1 | 1 | 1 | 2 | 2 | 2 | 0 | 0 | 3 | 0 | 1 | 1 |
| oligo27 | 63.3 | 21 | 1 | 3 | 0 | 1 | 1 | 0 | 1 | 3 | 1 | 1 | 2 | 1 | 2 | 1 | 2 | 0 |
| oligo28 | 63.5 | 21 | 0 | 0 | 2 | 1 | 1 | 2 | 4 | 0 | 1 | 3 | 2 | 2 | 0 | 2 | 0 | 0 |
| oligo29 | 64.0 | 22 | 0 | 2 | 2 | 2 | 1 | 0 | 3 | 1 | 3 | 3 | 0 | 2 | 0 | 2 | 1 | 1 | 0 |
| oligo30 | 65.5 | 29 | 4 | 2 | 1 | 1 | 1 | 4 | 1 | 2 | 2 | 1 | 0 | 0 | 2 | 1 | 0 | 4 |
| oligo31 | 66.5 | 25 | 2 | 3 | 1 | 2 | 1 | 0 | 3 | 1 | 0 | 1 | 2 | 2 | 4 | 1 | 0 | 1 |
| oligo32 | 67.0 | 21 | 3 | 1 | 1 | 2 | 0 | 0 | 1 | 0 | 2 | 0 | 3 | 2 | 2 | 0 | 2 | 1 |
| oligo33 | 69.0 | 27 | 1 | 2 | 1 | 4 | 2 | 1 | 0 | 1 | 1 | 0 | 0 | 1 | 4 | 1 | 1 | 6 |
| oligo34 | 69.0 | 25 | 1 | 1 | 1 | 2 | 1 | 1 | 1 | 2 | 0 | 1 | 1 | 3 | 3 | 3 | 1 | 2 |
| oligo35 | 69.0 | 25 | 1 | 0 | 2 | 2 | 1 | 1 | 1 | 2 | 0 | 1 | 1 | 3 | 3 | 3 | 1 | 2 |
| oligo36 | 69.5 | 26 | 3 | 2 | 2 | 1 | 0 | 1 | 3 | 1 | 2 | 0 | 0 | 3 | 3 | 2 | 1 | 1 |
| oligo37 | 71.5 | 25 | 1 | 0 | 0 | 2 | 0 | 1 | 4 | 2 | 0 | 3 | 4 | 1 | 2 | 3 | 1 | 0 |
| Total | | | 65 | 59 | 42 | 45 | 37 | 74 | 61 | 44 | 57 | 36 | 43 | 40 | 52 | 48 | 34 | 42 |

(* The slash indicates the sequence are given in antiparallel orientation; e.g., AC/TG means 5'-AC-3' is Watson-Crike base paired with 3'-TG-5')

<1-3> Establishment of an Equation for $T_m$ Calculation

The NN sequences and experimental $T_m$s for the reference data set were applied to an equation for $T_m$ calculation, thereby determining the values of the parameters included in the equation.

One of NN models using thermodynamic parameters $\Delta H°$ and $\Delta S°$ was used as the equation for $T_m$ calculation (see SantaLucia, J. Jr (2007) Physical principles and visual-OMP software for optimal PCR design. Methods Mol. Biol., 402, 3-34). The equation is represented by the following Equation I-1.

$$Tm = \frac{\Delta H° \times 1000}{\Delta S°} - 273.15 \qquad \text{Equation I-1}$$

wherein $T_m$ is the melting temperature of the oligonucleotide; $\Delta H°$ is the sum of the enthalpy changes; and $\Delta S°$ is the sum of the entropy changes.

In the above equation, $\Delta H°$ can be calculated by the sum of each NN parameter $\Delta H°_{NN}$, and $\Delta S°$ can be calculated by the sum of each NN parameter $\Delta S°_{NN}$, as shown in the following Equation II.

$$\Delta H° = \Sigma_{NN} (\text{each } \Delta H°_{NN}), \Delta S° = \Sigma_{NN} (\text{each } \Delta S°_{NN}) \qquad \text{Equation II}$$

Each of the values of the NN parameters was calculated by finding a value to minimize the sum of squared errors by least square method. Among sixteen (16) NN sequences, six (6) NN sequences were assumed to have the same parameter values as their complementary NN sequences (AA/TT=TT/AA; CA/GT=TG/AC, GT/CA=AC/TG, CT/GA=AG/TC, GA/CT=TC/AG, GG/CC=CC/GG)

The NN parameter values for each NN sequence which are determined using the thirty-seven (37) reference oligonucleotides are shown in Table 2 below.

TABLE 2

| Pair | AA/ TT | AT/ TA | AG/ TC | AC/ TG | TA/ AT | TT/ AA | TG/ AC | TC/ AG | GA/ CT | GT/ CA | GG/ CC | GC/ CG | CA/ GT | CT/ GA | CG/ GC | CC/ GG |
|---|---|---|---|---|---|---|---|---|---|---|---|---|---|---|---|---|
| $\Delta S°$ | -27.3 | -24.6 | -25.6 | -24.0 | -28.6 | -27.3 | -24.8 | -23.6 | -23.6 | -24.0 | -23.9 | -23.9 | -24.8 | -25.6 | -25.2 | -23.9 |
| $\Delta H°$ | -8.9 | -8.7 | -8.3 | -9.2 | -8.1 | -8.9 | -8.2 | -7.7 | -7.7 | -9.2 | -8.2 | -9.0 | -8.2 | -8.3 | -7.5 | -8.2 |

(*rounded to the nearest tenth)

<1-4> $T_m$ Prediction of Oligonucleotides Using the Equation Having the NN Parameter Values Optimized for the Specific Reaction Environment The Equation I-1 having the values of the NN parameters determined in Example <1-3> was used to calculate the predicted $T_m$s of the remaining fifty-eight (58) oligonucleotides. Then, the predicted $T_m$ of each oligonucleotide was compared with the experimental $T_m$ in Example 1 to evaluate the $T_m$ prediction performance of the Equation I-1.

The experimental $T_m$, the NN parameters, the predicted $T_m$, and the error between the predicted $T_m$ and the experimental $T_m$ of each of the 58 oligonucleotides (oligo 38 to 95) are shown in Table 3 below.

TABLE 3

| | Ex. T$_m$ | Total $\Delta H°$ | Total $\Delta S°$ | Predicted T$_m$ | \|Predicted T$_m$ - experimental T$_m$\| |
|---|---|---|---|---|---|
| oligo38 | 52.5 | -195.2 | -592.3 | 56.4 | 3.9 |
| oligo39 | 53.3 | -152.6 | -458.3 | 59.7 | 6.4 |
| oligo40 | 54.0 | -162.6 | -488.8 | 59.5 | 5.5 |
| oligo41 | 55.3 | -196.1 | -597.4 | 55.0 | 0.3 |
| oligo42 | 55.8 | -179.3 | -541.2 | 58.2 | 2.4 |
| oligo43 | 56.0 | -204.3 | -616.3 | 58.4 | 2.4 |
| oligo44 | 56.5 | -230.7 | -701.3 | 55.8 | 0.7 |

TABLE 3-continued

| | Ex. $T_m$ | Total ΔH° | Total ΔS° | Predicted $T_m$ | \|Predicted $T_m$ − experimental $T_m$\| |
|---|---|---|---|---|---|
| oligo45 | 56.9 | −170.8 | −512.7 | 60.0 | 3.1 |
| oligo46 | 57.0 | −159.2 | −476.9 | 60.6 | 3.6 |
| oligo47 | 57.0 | −175.5 | −529.0 | 58.6 | 1.6 |
| oligo48 | 57.5 | −205.2 | −620.4 | 57.7 | 0.2 |
| oligo49 | 58.0 | −140.0 | −420.7 | 59.7 | 1.7 |
| oligo50 | 58.0 | −148.5 | −442.1 | 62.6 | 4.6 |
| oligo51 | 58.0 | −150.8 | −450.9 | 61.4 | 3.4 |
| oligo52 | 58.0 | −187.6 | −561.1 | 61.3 | 3.3 |
| oligo53 | 58.0 | −177.3 | −531.2 | 60.7 | 2.7 |
| oligo54 | 58.0 | −148.5 | −442.1 | 62.6 | 4.6 |
| oligo55 | 58.0 | −188.5 | −565.2 | 60.4 | 2.4 |
| oligo56 | 58.3 | −149.4 | −443.1 | 64.0 | 5.7 |
| oligo57 | 58.5 | −177.4 | −529.5 | 61.9 | 3.4 |

As shown in Table 3, the $T_m$s of the 58 oligonucleotides were predicted with the mean absolute error of 2.9, the sum of absolute error of 165.5, and the sum of squared error of 647.7.

<1-5> $T_m$ Prediction of Oligonucleotides Using the Equation Having Known NN Parameter Values The $T_m$ prediction performance of the equation having the NN parameter values determined in Example <1-4> was compared with the equation having known NN parameter values (SantaLucia & Hicks (2004), Annu. Rev. Biophys. Biomol. Struct 33: 415-440).

The known NN parameter values are shown in Table 4 below.

TABLE 4

| Pair | AA/TT | AT/TA | AG/TC | AC/TG | TA/AT | TT/AA | TG/AC | TC/AG | GA/CT | GT/CA | GG/CC | GC/CG | CA/GT | CT/GA | CG/GC | CC/GG |
|---|---|---|---|---|---|---|---|---|---|---|---|---|---|---|---|---|
| ΔS° | −21.3 | −20.4 | −21.0 | −22.4 | −21.3 | −21.3 | −22.7 | −22.2 | −22.2 | −22.4 | −19.9 | −24.4 | −22.7 | −21.0 | −27.2 | −19.9 |
| ΔH° | −7.6 | −7.2 | −7.8 | −8.4 | −7.2 | −7.6 | −8.5 | −8.2 | −8.2 | −8.4 | −8.0 | −9.8 | −8.5 | −7.8 | −10.6 | −8.0 |

TABLE 3-continued

| | Ex. $T_m$ | Total ΔH° | Total ΔS° | Predicted $T_m$ | \|Predicted $T_m$ − experimental $T_m$\| |
|---|---|---|---|---|---|
| oligo58 | 58.5 | −185.6 | −554.3 | 61.8 | 3.3 |
| oligo59 | 59.0 | −239.9 | −725.3 | 57.6 | 1.4 |
| oligo60 | 60.0 | −150.2 | −447.6 | 62.4 | 2.4 |
| oligo61 | 60.0 | −161.5 | −479.7 | 63.4 | 3.4 |
| oligo62 | 60.0 | −144.1 | −423.0 | 67.6 | 7.6 |
| oligo63 | 60.0 | −248.1 | −749.1 | 58.0 | 2.0 |
| oligo64 | 60.5 | −153.0 | −450.3 | 66.7 | 6.2 |
| oligo65 | 60.5 | −196.6 | −585.0 | 62.9 | 2.4 |
| oligo66 | 60.5 | −230.2 | −696.8 | 57.2 | 3.3 |
| oligo67 | 60.8 | −204.6 | −613.1 | 60.5 | 0.3 |
| oligo68 | 61.4 | −204.6 | −614.4 | 59.8 | 1.6 |
| oligo69 | 61.5 | −171.1 | −505.6 | 65.3 | 3.8 |
| oligo70 | 61.5 | −265.0 | −798.6 | 58.6 | 2.9 |
| oligo71 | 61.8 | −179.8 | −536.6 | 61.9 | 0.1 |
| oligo72 | 62.0 | −161.3 | −475.8 | 65.9 | 3.9 |
| oligo73 | 62.0 | −179.2 | −534.2 | 62.4 | 0.4 |
| oligo74 | 62.5 | −182.7 | −549.8 | 59.2 | 3.3 |
| oligo75 | 62.5 | −204.9 | −614.6 | 60.2 | 2.3 |
| oligo76 | 63.0 | −169.3 | −499.6 | 65.7 | 2.7 |
| oligo77 | 63.0 | −170.7 | −499.9 | 68.4 | 5.4 |
| oligo78 | 63.0 | −238.3 | −720.7 | 57.6 | 5.4 |
| oligo79 | 63.5 | −194.7 | −579.0 | 63.1 | 0.4 |
| oligo80 | 63.5 | −179.6 | −527.1 | 67.5 | 4.0 |
| oligo81 | 63.8 | −213.6 | −639.2 | 61.0 | 2.8 |
| oligo82 | 64.0 | −171.2 | −503.1 | 67.1 | 3.1 |
| oligo83 | 64.0 | −168.0 | −498.4 | 63.9 | 0.1 |
| oligo84 | 64.0 | −178.2 | −526.8 | 65.1 | 1.1 |
| oligo85 | 64.0 | −188.5 | −554.4 | 66.8 | 2.8 |
| oligo86 | 65.0 | −194.0 | −578.7 | 62.2 | 2.8 |
| oligo87 | 65.0 | −169.4 | −502.0 | 64.2 | 0.8 |
| oligo88 | 65.5 | −187.1 | −554.1 | 64.5 | 1.0 |
| oligo89 | 65.5 | −205.3 | −607.6 | 64.7 | 0.8 |
| oligo90 | 65.5 | −179.4 | −527.1 | 67.2 | 1.7 |
| oligo91 | 66.5 | −228.4 | −678.2 | 63.7 | 2.8 |
| oligo92 | 69.0 | −221.7 | −650.9 | 67.4 | 1.6 |
| oligo93 | 69.0 | −194.2 | −574.3 | 65.0 | 4.0 |
| oligo94 | 69.5 | −202.6 | −599.7 | 64.6 | 4.9 |
| oligo95 | 70.0 | −194.1 | −573.6 | 65.2 | 4.8 |
| Mean Absolute Error | | | | | 2.9 |
| Sum of Absolute Errors | | | | | 165.5 |
| Sum of Squared Errors | | | | | 647.7 |

(*rounded to the nearest tenth)

The predicted $T_m$s of the 58 oligonucleotides were calculated in the same manner to Example <1-4> except for using the equation having the known NN parameter values.

Afterwards, the predicted $T_m$ of each oligonucleotide was compared with the experimental $T_m$ to evaluate the $T_m$ prediction performance of the known values of the NN parameters.

The experimental $T_m$, the NN parameters, the predicted $T_m$, and the error between the predicted $T_m$ and the experimental $T_m$ of each of the 58 oligonucleotides (oligo 38 to 95) are shown in Table 5 below.

TABLE 5

| | Ex. $T_m$ | Total ΔH° | Total ΔS° | Predicted $T_m$ | \|Predicted $T_m$ − experimental $T_m$\| |
|---|---|---|---|---|---|
| oligo38 | 52.5 | −178.5 | −494.8 | 87.6 | 35.1 |
| oligo39 | 53.3 | −146.1 | −395.1 | 96.6 | 43.3 |
| oligo40 | 54.0 | −152.4 | −413.8 | 95.1 | 41.1 |
| oligo41 | 55.3 | −180.4 | −495.9 | 90.6 | 35.3 |
| oligo42 | 55.8 | −163.6 | −446.7 | 93.1 | 37.3 |
| oligo43 | 56.0 | −186.9 | −517.2 | 88.2 | 32.2 |
| oligo44 | 56.5 | −208.9 | −580.0 | 87.0 | 30.5 |
| oligo45 | 56.9 | −160.4 | −433.7 | 96.7 | 39.8 |
| oligo46 | 57.0 | −152.6 | −410.6 | 98.5 | 41.5 |
| oligo47 | 57.0 | −167.5 | −457.9 | 92.7 | 35.7 |
| oligo48 | 57.5 | −189.3 | −519.5 | 91.2 | 33.7 |
| oligo49 | 58.0 | −145.2 | −386.0 | 103.0 | 45.0 |
| oligo50 | 58.0 | −150.5 | −401.1 | 101.3 | 43.3 |
| oligo51 | 58.0 | −149.4 | −400.2 | 100.2 | 42.2 |
| oligo52 | 58.0 | −173.0 | −472.4 | 93.1 | 35.1 |
| oligo53 | 58.0 | −169.8 | −459.9 | 96.1 | 38.1 |
| oligo54 | 58.0 | −150.2 | −401.1 | 101.3 | 43.3 |
| oligo55 | 58.0 | −172.0 | −469.1 | 93.5 | 35.5 |
| oligo56 | 58.3 | −147.1 | −393.0 | 101.2 | 42.9 |
| oligo57 | 58.5 | −168.6 | −456.8 | 95.9 | 37.4 |
| oligo58 | 58.5 | −176.7 | −481.2 | 94.1 | 35.6 |
| oligo59 | 59.0 | −217.3 | −602.4 | 87.6 | 28.6 |
| oligo60 | 60.0 | −150.3 | −400.0 | 102.6 | 42.6 |
| oligo61 | 60.0 | −153.9 | −413.3 | 99.2 | 39.2 |
| oligo62 | 60.0 | −141.2 | −374.4 | 104.0 | 44.0 |
| oligo63 | 60.0 | −225.3 | −622.3 | 88.9 | 28.9 |
| oligo64 | 60.5 | −148.8 | −395.7 | 102.9 | 42.4 |
| oligo65 | 60.5 | −182.8 | −496.8 | 94.8 | 34.3 |
| oligo66 | 60.5 | −212.9 | −584.0 | 91.4 | 30.9 |
| oligo67 | 60.8 | −190.5 | −518.3 | 94.4 | 33.6 |
| oligo68 | 61.4 | −188.0 | −512.3 | 93.8 | 32.4 |

TABLE 5-continued

| | Ex. $T_m$ | Total ΔH ° | Total ΔS ° | Predicted $T_m$ | |Predicted $T_m$ − experimental $T_m$| |
|---|---|---|---|---|---|
| oligo69 | 61.5 | −161.9 | −434.6 | 99.4 | 37.9 |
| oligo70 | 61.5 | −241.0 | −665.4 | 89.0 | 27.5 |
| oligo71 | 61.8 | −170.2 | −458.1 | 98.4 | 36.6 |
| oligo72 | 62.0 | −156.6 | −416.7 | 102.7 | 40.7 |
| oligo73 | 62.0 | −169.1 | −455.9 | 97.8 | 35.8 |
| oligo74 | 62.5 | −181.0 | −484.1 | 100.7 | 38.2 |
| oligo75 | 62.5 | −191.1 | −518.9 | 95.1 | 32.6 |
| oligo76 | 63.0 | −163.4 | −436.9 | 100.8 | 37.8 |
| oligo77 | 63.0 | −163.6 | −437.1 | 101.1 | 38.1 |
| oligo78 | 63.0 | −220.9 | −603.9 | 92.6 | 29.6 |
| oligo79 | 63.5 | −186.2 | −502.2 | 97.6 | 34.1 |
| oligo80 | 63.5 | −171.2 | −458.4 | 100.3 | 36.8 |
| oligo81 | 63.8 | −198.3 | −539.3 | 94.5 | 30.7 |
| oligo82 | 64.0 | −167.1 | −446.7 | 100.9 | 36.9 |
| oligo83 | 64.0 | −163.8 | −436.7 | 101.9 | 37.9 |
| oligo84 | 64.0 | −171.0 | −458.2 | 100.0 | 36.0 |
| oligo85 | 64.0 | −178.8 | −479.7 | 99.6 | 35.6 |
| oligo86 | 65.0 | −187.6 | −506.4 | 97.3 | 32.3 |
| oligo87 | 65.0 | −167.8 | −448.8 | 100.7 | 35.7 |
| oligo88 | 65.5 | −178.6 | −479.5 | 99.3 | 33.8 |
| oligo89 | 65.5 | −193.2 | −521.4 | 97.4 | 31.9 |
| oligo90 | 65.5 | −172.6 | −460.4 | 101.7 | 36.2 |
| oligo91 | 66.5 | −218.8 | −589.5 | 98.0 | 31.5 |
| oligo92 | 69.0 | −214.4 | −571.7 | 101.9 | 32.9 |
| oligo93 | 69.0 | −192.8 | −509.2 | 105.5 | 36.5 |
| oligo94 | 69.5 | −200.8 | −531.7 | 104.5 | 35.0 |
| oligo95 | 70.0 | −193.5 | −510.9 | 105.6 | 35.6 |
| Mean Absolute Error | | | | | 36.3 |
| Sum of Absolute Errors | | | | | 2105.4 |
| Sum of Squared Errors | | | | | 77454.9 |

(*rounded to the nearest tenth)

As shown in Table 5, the $T_m$s of the 58 oligonucleotides were predicted using known NN parameter values, with the mean absolute error of 36.3, the sum of absolute error of 2105.4, and the sum of squared error of 77454.9.

The $T_m$ prediction performance of the equation having the NN parameter values optimized for the specific reaction environment according to the present invention (Table 3) was compared with that of the equation having the known NN parameter values (Table 5). As a result, it was found that the use of the equation having the NN parameter values (Table 3) optimized for a specific reaction environment according to the present invention reduced the mean absolute error by −33.4, the sum of absolute error by −1939.2, and the sum of squared error by of −76807.2.

The results demonstrate that using the optimized values of the NN parameters for a specific reaction environment allows for prediction of a more accurate $T_m$ compared to using the known NN parameter values. The known NN parameter values are optimized for a fixed reaction environment (1M NaCl, pH 7), thereby resulting in unsuitability for use in different reaction environments.

Furthermore, for a sophisticated comparison between the NN parameter values determined according to the present invention and the known NN parameter values, the slope of the trend line and the coefficient of determination $R^2$ were determined in a scatter plot indicating the correlation between the experimental $T_m$ and the predicted $T_m$.

Figure 2:
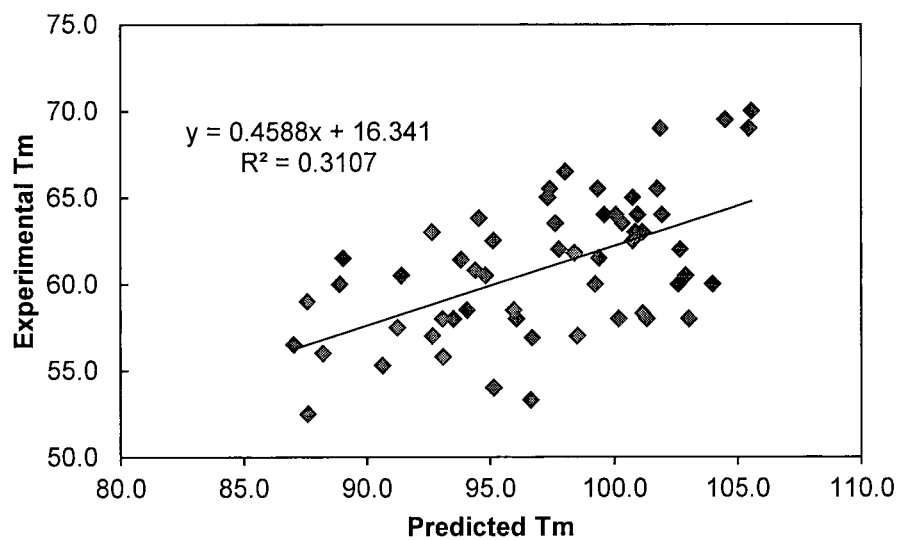
FIG. 2 shows (A) a scatter plot illustrating the correlation between the experimental $T_m$ and the predicted $T_m$ calculated using the conventional known NN parameters, and (B) a scatter plot illustrating the correlation between the experimental $T_m$ and the predicted $T_m$ calculated using the NN parameters of the present invention.
Figure 2:
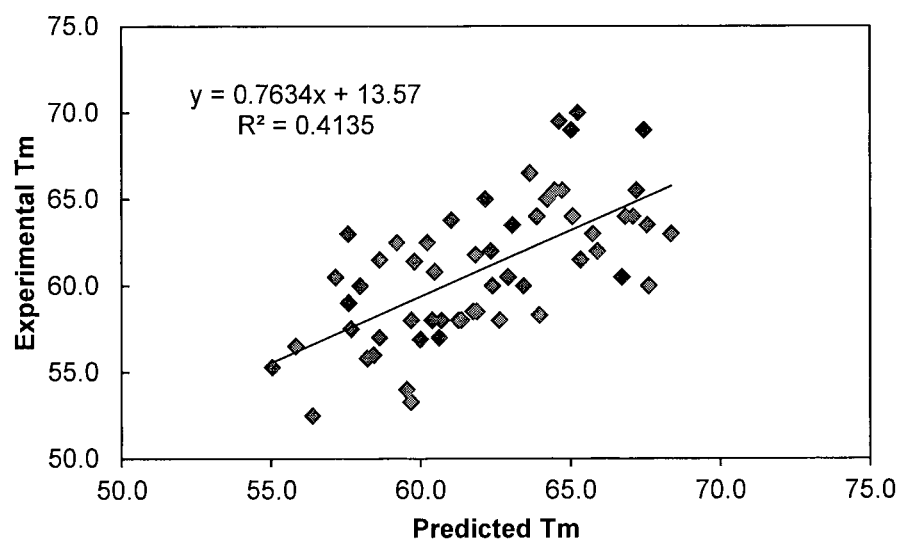

The results are shown in FIG. 2.

As shown in FIG. 2, the $T_m$ prediction using the known NN parameter values (Table 5) showed the slope of the trend line of 0.4588 and the coefficient of determination $R^2$ of 0.3107, indicating a low correlation between the predicted $T_m$ and the experimental $T_m$. In contrast, the $T_m$ prediction using the NN parameter values according to the present invention showed the slope of the trend line of 0.7634 and the coefficient of determination $R^2$ of 0.4135, indicating a high correlation between the predicted $T_m$ and the experimental $T_m$.

Considering that a higher correlation is associated with a higher similarity between the predicted $T_m$ and the experimental $T_m$, the results demonstrate that using the NN parameter values optimized for the reaction environment makes it possible to more accurately predict the $T_m$ of the oligonucleotide.

Example 2: Prediction of Melting Temperature of Oligonucleotide Using a Modified $T_m$ Prediction Model In this Example, it was verified whether the accuracy of $T_m$ prediction of the oligonucleotide can be improved by using other equations than Equation I-1.

In addition to the NN parameters, one or more additional parameters were introduced into Equation I-1 to generate modified equations for $T_m$ calculation, and then the $T_m$ prediction performances of these equations were determined.

Specifically, the following four (4) equations for $T_m$ calculation were used: (i) an equation including only NN parameters (control group); (ii) an equation including a first additional parameter α in addition to the NN parameters; (iii) an equation including a second additional parameter β in addition to the NN parameters; and (iv) an equation including the first and second additional parameters α and β in addition to the NN parameters.

As in Example 1, a reference data set comprising thirty-seven (37) reference oligonucleotides was used to determine the parameter values that minimized the sum of squared errors for each of the four (4) equations. Then, each of the four equations having the parameter values was used to calculate the predicted $T_m$s of fifty-eight (58) oligonucleotides.

<2-1> $T_m$ Prediction of Oligonucleotide Using an Equation Including Only NN Parameters Equation I-1 was used as an equation for $T_m$ calculation, including only the NN parameters. The $T_m$s of fifty-eight (58) oligonucleotides were predicted using Equation I-1 having the NN parameter values as shown in Table 2. The predicted $T_m$s of the 58 oligonucleotides are shown in Table 3.

<2-2> $T_m$ Prediction Using an Equation Including the NN Parameters and the Parameter α

A first additional parameter α was added to Equation I-1 to generate a modified equation for $T_m$ calculation, Equation III-1.

$$Tm_{(\alpha)} = \frac{\Delta H° \times 1000}{\Delta S° + \alpha} - 273.15 \qquad \text{Equation III-1}$$

Thirty-seven (37) reference oligonucleotides of Example <1-2> were used to determine the values of the NN parameters and the value of the parameter α for Equation III-1 above.

The values of the NN parameters determined were shown in Table 6, and the value of the parameter α determined was −24.9.

TABLE 6

| Pair | AA/TT | AT/TA | AG/TC | AC/TG | TA/AT | TT/AA | TG/AC | TC/AG | GA/CT | GT/CA | GG/CC | GC/CG | CA/GT | CT/GC | CG/GA | CC/GG |
|---|---|---|---|---|---|---|---|---|---|---|---|---|---|---|---|---|
| ΔS° | −23.5 | −25.1 | −23.8 | −23.4 | −25.2 | −23.5 | −23.9 | −25.4 | −25.4 | −23.4 | −21.3 | −26.1 | −23.9 | −23.8 | −24.5 | −21.3 |
| ΔH° | −8.0 | −8.1 | −8.3 | −8.2 | −8.0 | −8.0 | −8.8 | −8.9 | −8.9 | −8.2 | −7.9 | −9.4 | −8.8 | −8.3 | −9.2 | −7.9 |

(*rounded to the nearest tenth)

The Equation III-1 having the parameter values above was used to calculate the predicted $T_m$s of fifty-eight (58) oligonucleotides (oligo 38-95).

The experimental $T_m$, the NN parameters, the predicted $T_m$, and the error between the predicted $T_m$ and the experimental $T_m$ of each of the 58 oligonucleotides (oligo 38 to 95) are shown in Table 7 below.

TABLE 7

| | Ex. $T_m$ | Total ΔH° | Total ΔS° | Predicted $T_m$ | |Predicted $T_m$ − experimental $T_m$| |
|---|---|---|---|---|---|
| oligo38 | 52.5 | −190.6 | −559.3 | 53.1 | 0.6 |
| oligo39 | 53.3 | −150.5 | −431.7 | 56.4 | 3.1 |
| oligo40 | 54.0 | −159.0 | −458.1 | 56.0 | 2.0 |
| oligo41 | 55.3 | −188.7 | −549.8 | 55.2 | 0.1 |
| oligo42 | 55.8 | −171.9 | −496.7 | 56.5 | 0.7 |
| oligo43 | 56.0 | −198.8 | −582.7 | 54.1 | 1.9 |
| oligo44 | 56.5 | −222.6 | −653.3 | 55.1 | 1.4 |
| oligo45 | 56.9 | −166.9 | −479.4 | 57.8 | 0.9 |
| oligo46 | 57.0 | −160.2 | −456.1 | 59.9 | 2.9 |
| oligo47 | 57.0 | −176.3 | −511.1 | 55.8 | 1.2 |
| oligo48 | 57.5 | −199.5 | −579.1 | 57.2 | 0.3 |
| oligo49 | 58.0 | −145.9 | −412.0 | 60.9 | 2.9 |
| oligo50 | 58.0 | −154.0 | −438.3 | 59.3 | 1.3 |
| oligo51 | 58.0 | −154.0 | −437.8 | 59.7 | 1.7 |
| oligo52 | 58.0 | −181.8 | −524.7 | 57.7 | 0.3 |
| oligo53 | 58.0 | −178.4 | −511.9 | 59.1 | 1.1 |
| oligo54 | 58.0 | −154.0 | −438.3 | 59.3 | 1.3 |
| oligo55 | 58.0 | −180.1 | −520.1 | 57.4 | 0.6 |
| oligo56 | 58.3 | −151.9 | −429.7 | 61.1 | 2.8 |
| oligo57 | 58.5 | −176.8 | −506.8 | 59.3 | 0.8 |
| oligo58 | 58.5 | −184.4 | −531.2 | 58.5 | 0.0 |
| oligo59 | 59.0 | −230.9 | −676.7 | 55.9 | 3.1 |
| oligo60 | 60.0 | −154.6 | −436.5 | 61.9 | 1.9 |
| oligo61 | 60.0 | −158.6 | −451.9 | 59.6 | 0.4 |
| oligo62 | 60.0 | −144.3 | −406.0 | 61.7 | 1.7 |
| oligo63 | 60.0 | −238.8 | −698.1 | 57.1 | 2.9 |
| oligo64 | 60.5 | −152.3 | −429.5 | 62.1 | 1.6 |
| oligo65 | 60.5 | −191.3 | −550.8 | 59.1 | 1.4 |
| oligo66 | 60.5 | −224.7 | −651.8 | 59.0 | 1.5 |
| oligo67 | 60.8 | −199.4 | −574.7 | 59.5 | 1.3 |
| oligo68 | 61.4 | −197.4 | −569.3 | 59.0 | 2.4 |
| oligo69 | 61.5 | −166.6 | −473.7 | 61.0 | 0.5 |
| oligo70 | 61.5 | −255.6 | −747.1 | 58.0 | 3.5 |
| oligo71 | 61.8 | −176.3 | −505.5 | 59.3 | 2.5 |
| oligo72 | 62.0 | −160.6 | −453.3 | 62.7 | 0.7 |
| oligo73 | 62.0 | −174.6 | −498.9 | 60.3 | 1.7 |
| oligo74 | 62.5 | −187.2 | −533.4 | 62.2 | 0.3 |
| oligo75 | 62.5 | −198.8 | −572.7 | 59.5 | 3.0 |
| oligo76 | 63.0 | −168.3 | −476.0 | 62.8 | 0.2 |
| oligo77 | 63.0 | −167.6 | −474.0 | 62.7 | 0.3 |
| oligo78 | 63.0 | −232.6 | −673.1 | 60.2 | 2.8 |
| oligo79 | 63.5 | −194.5 | −556.6 | 61.3 | 2.2 |
| oligo80 | 63.5 | −175.6 | −497.5 | 62.9 | 0.6 |
| oligo81 | 63.8 | −206.8 | −597.8 | 59.0 | 4.8 |
| oligo82 | 64.0 | −169.9 | −479.5 | 63.7 | 0.3 |
| oligo83 | 64.0 | −170.1 | −480.8 | 63.2 | 0.8 |
| oligo84 | 64.0 | −176.3 | −499.5 | 63.0 | 1.0 |
| oligo85 | 64.0 | −183.6 | −521.0 | 63.1 | 0.9 |
| oligo86 | 65.0 | −194.2 | −554.7 | 61.9 | 3.1 |
| oligo87 | 65.0 | −169.6 | −479.1 | 63.4 | 1.6 |
| oligo88 | 65.5 | −184.3 | −523.0 | 63.2 | 2.3 |
| oligo89 | 65.5 | −199.7 | −571.3 | 61.8 | 3.7 |
| oligo90 | 65.5 | −176.8 | −500.2 | 63.6 | 1.9 |
| oligo91 | 66.5 | −227.7 | −647.3 | 65.6 | 0.9 |
| oligo92 | 69.0 | −220.6 | −623.0 | 67.3 | 1.7 |
| oligo93 | 69.0 | −195.4 | −548.9 | 67.5 | 1.5 |
| oligo94 | 69.5 | −204.1 | −574.1 | 67.6 | 1.9 |
| oligo95 | 70.0 | −195.9 | −549.0 | 68.3 | 1.7 |
| Mean Absolute Error | | | | | 1.6 |
| Sum of Absolute Errors | | | | | 92.3 |
| Sum of Squared Errors | | | | | 188.7 |

(*rounded to the nearest tenth)

As shown in Table 7, the $T_m$s of the 58 oligonucleotides were predicted using Equation III-1, with the mean absolute error of 1.6, the sum of absolute error of 92.3, and the sum of squared error of 188.7.

<2-3> $T_m$ Prediction Using an Equation Including the NN Parameters and the Parameter β

A second additional parameter β was added to Equation I-1 to generate a modified equation for $T_m$ calculation, Equation IV-1.

$$Tm = \frac{\Delta H° \times 1000}{\Delta S°} + \beta \ln(\text{length}) - 273.15 \quad \text{Equation IV-1}$$

Thirty-seven (37) reference oligonucleotides of Example <1-2> were used to determine the values of the NN parameters and the value of the parameter β for Equation IV-1 above.

The values of the NN parameters determined were shown in Table 8, and the value of the parameter β determined was 5.00.

TABLE 8

| Pair | AA/TT | AT/TA | AG/TC | AC/TG | TA/AT | TT/AA | TG/AC | TC/AG | GA/CT | GT/CA | GG/CC | GC/CG | CA/GT | CT/GC | CG/GA | CC/GG |
|---|---|---|---|---|---|---|---|---|---|---|---|---|---|---|---|---|
| ΔS° | −27.2 | −26.2 | −24.6 | −23.4 | −27.0 | −27.2 | −25.1 | −25.1 | −25.1 | −23.4 | −24.2 | −25.4 | −25.1 | −24.6 | −24.6 | −24.2 |
| ΔH° | −8.4 | −8.6 | −7.6 | −8.4 | −7.2 | −8.4 | −7.9 | −7.9 | −7.9 | −8.4 | −8.0 | −9.0 | −7.9 | −7.6 | −7.1 | −8.0 |

(*rounded to the nearest tenth)

The Equation IV-1 having the parameter values above was used to calculate the predicted $T_m$s of fifty-eight (58) oligonucleotides (oligo 38-95).

The experimental $T_m$, the NN parameters, the predicted $T_m$, and the error between the predicted $T_m$ and the experimental $T_m$ of each of the 58 oligonucleotides (oligo 38 to 95) are shown in Table 9 below.

TABLE 9

| Ex. | Total ΔH° | Total ΔS° | Predicted $T_m$ | \|Predicted $T_m$ − experimental $T_m$\| |
|---|---|---|---|---|
| oligo1 | 52.5 | −186.6 | −595.7 | 52.5 | 3.5 |
| oligo2 | 53.3 | −146.2 | −460.7 | 53.3 | 5.5 |
| oligo3 | 54.0 | −155.3 | −490.2 | 54.0 | 4.7 |
| oligo4 | 55.3 | −186.5 | −596.9 | 55.3 | 0.1 |
| oligo5 | 55.8 | −172.1 | −545.4 | 55.8 | 2.1 |
| oligo6 | 56.0 | −195.1 | −619.1 | 56.0 | 2.0 |
| oligo7 | 56.5 | −220.4 | −704.5 | 56.5 | 0.2 |
| oligo8 | 56.9 | −163.3 | −514.5 | 56.9 | 2.6 |
| oligo9 | 57.0 | −154.3 | −484.7 | 57.0 | 3.2 |
| oligo10 | 57.0 | −169.4 | −536.4 | 57.0 | 1.2 |
| oligo11 | 57.5 | −195.3 | −620.2 | 57.5 | 0.3 |
| oligo12 | 58.0 | −135.8 | −426.5 | 58.0 | 1.6 |
| oligo13 | 58.0 | −144.4 | −450.7 | 58.0 | 3.9 |
| oligo14 | 58.0 | −145.7 | −456.5 | 58.0 | 2.8 |
| oligo15 | 58.0 | −180.3 | −566.5 | 58.0 | 2.7 |
| oligo16 | 58.0 | −170.7 | −536.6 | 58.0 | 2.4 |
| oligo17 | 58.0 | −144.4 | −450.7 | 58.0 | 3.9 |
| oligo18 | 58.0 | −180.6 | −568.8 | 58.0 | 2.0 |
| oligo19 | 58.3 | −145.2 | −451.3 | 58.3 | 4.9 |
| oligo20 | 58.5 | −170.5 | −534.2 | 58.5 | 3.0 |
| oligo21 | 58.5 | −178.9 | −561.0 | 58.5 | 2.9 |
| oligo22 | 59.0 | −228.8 | −727.9 | 59.0 | 0.9 |
| oligo23 | 60.0 | −145.1 | −452.7 | 60.0 | 2.0 |
| oligo24 | 60.0 | −152.2 | −474.6 | 60.0 | 2.6 |
| oligo25 | 60.0 | −137.4 | −422.8 | 60.0 | 6.3 |
| oligo26 | 60.0 | −236.8 | −752.1 | 60.0 | 1.3 |
| oligo27 | 60.5 | −145.9 | −450.0 | 60.5 | 5.2 |
| oligo28 | 60.5 | −189.2 | −591.8 | 60.5 | 2.0 |
| oligo29 | 60.5 | −219.3 | −697.2 | 60.5 | 2.5 |
| oligo30 | 60.8 | −195.7 | −616.1 | 60.8 | 0.3 |
| oligo31 | 61.4 | −196.1 | −618.6 | 61.4 | 1.4 |
| oligo32 | 61.5 | −161.9 | −502.0 | 61.5 | 3.0 |
| oligo33 | 61.5 | −253.4 | −803.4 | 61.5 | 2.0 |
| oligo34 | 61.8 | −172.3 | −539.8 | 61.8 | 0.4 |
| oligo35 | 62.0 | −153.5 | −474.6 | 62.0 | 3.2 |
| oligo36 | 62.0 | −169.1 | −529.0 | 62.0 | 0.0 |
| oligo37 | 62.5 | −175.1 | −551.8 | 62.5 | 2.6 |
| oligo38 | 62.5 | −193.4 | −609.4 | 62.5 | 2.1 |
| oligo39 | 63.0 | −160.8 | −497.8 | 63.0 | 2.2 |
| oligo40 | 63.0 | −161.4 | −496.1 | 63.0 | 4.4 |
| oligo41 | 63.0 | −227.2 | −721.4 | 63.0 | 4.3 |
| oligo42 | 63.5 | −187.1 | −584.2 | 63.5 | 0.5 |
| oligo43 | 63.5 | −169.8 | −523.3 | 63.5 | 3.3 |
| oligo44 | 63.8 | −202.1 | −635.6 | 63.8 | 2.7 |
| oligo45 | 64.0 | −164.4 | −507.0 | 64.0 | 2.4 |
| oligo46 | 64.0 | −162.3 | −504.6 | 64.0 | 0.3 |
| oligo47 | 64.0 | −169.3 | −525.0 | 64.0 | 0.7 |
| oligo48 | 64.0 | −178.2 | −550.5 | 64.0 | 2.3 |
| oligo49 | 65.0 | −186.0 | −582.2 | 65.0 | 2.7 |
| oligo50 | 65.0 | −162.0 | −503.2 | 65.0 | 0.9 |
| oligo51 | 65.5 | −177.7 | −552.2 | 65.5 | 1.2 |
| oligo52 | 65.5 | −194.1 | −603.7 | 65.5 | 1.0 |
| oligo53 | 65.5 | −170.3 | −525.2 | 65.5 | 1.1 |
| oligo54 | 66.5 | −218.4 | −680.2 | 66.5 | 1.9 |
| oligo55 | 69.0 | −213.0 | −656.1 | 69.0 | 1.1 |
| oligo56 | 69.0 | −185.2 | −573.5 | 69.0 | 3.4 |
| oligo57 | 69.5 | −193.9 | −601.2 | 69.5 | 4.0 |
| oligo58 | 70.0 | −185.5 | −573.9 | 70.0 | 4.1 |
| Mean Absolute Error | | | | 2.4 |
| Sum of Absolute Errors | | | | 137.9 |
| Sum of Squared Errors | | | | 414.1 |

(*rounded to the nearest tenth)

As shown in Table 9, the $T_m$s of the 58 oligonucleotides were predicted using Equation IV-1, with the mean absolute error of 2.4, the sum of absolute error of 137.9, and the sum of squared error of 414.1.

<2-4> $T_m$ Prediction Using an Equation Including the NN Parameters, the Parameters α and β

A first additional parameter α and a second additional parameter β were added to Equation I-1 to generate a modified equation for $T_m$ calculation, Equation V-1.

$$Tm = \frac{\Delta H° \times 1000}{\Delta S° + \alpha} + \beta \ln(\text{length}) - 273.15 \quad \text{Equation V-1}$$

Thirty-seven (37) reference oligonucleotides of Example <1-2> were used to determine the values of the NN parameters, the value of the parameter α, and the value of the parameter β for Equation V-1 above.

The values of the NN parameters determined were as shown in Table 10, and the values of the parameters α and β determined were −40.4 and 2.6, respectively.

TABLE 10

| Pair | AA/TT | AT/TA | AG/TC | AC/TG | TA/AT | TT/AA | TG/AC | TC/AG | GA/CT | GT/CA | GG/CC | GC/CG | CA/GT | CT/GA | CG/GC | CC/GG |
|---|---|---|---|---|---|---|---|---|---|---|---|---|---|---|---|---|
| ΔS° | −23.8 | −24.7 | −23.7 | −23.3 | −25.4 | −23.8 | −23.9 | −25.5 | −25.5 | −23.3 | −21.5 | −25.9 | −23.9 | −23.7 | −24.2 | −21.5 |
| ΔH° | −8.1 | −8.3 | −8.5 | −8.4 | −7.8 | −8.1 | −8.7 | −8.8 | −8.8 | −8.4 | −8.0 | −9.4 | −8.7 | −8.5 | −9.3 | −8.0 |

(*rounded to the nearest tenth)

The Equation V-1 having the parameter values above was used to calculate the predicted $T_m$s of fifty-eight (58) oligonucleotides (oligo 38-95).

The experimental $T_m$, the NN parameters, the predicted $T_m$, and the error between the predicted $T_m$ and the experimental $T_m$ of each of the 58 oligonucleotides (oligo 38 to 95) are shown in Table 11 below.

TABLE 11

| | Ex. $T_m$ | Total $\Delta H°$ | Total $\Delta S°$ | Predicted $T_m$ | \|Predicted $T_m$ – experimental $T_m$\| |
|---|---|---|---|---|---|
| oligo1 | 52.5 | −191.8 | −560.0 | 54.5 | 2.0 |
| oligo2 | 53.3 | −151.2 | −432.2 | 54.4 | 1.1 |
| oligo3 | 54.0 | −159.9 | −458.7 | 55.0 | 1.0 |
| oligo4 | 55.3 | −190.3 | −551.4 | 56.7 | 1.4 |
| oligo5 | 55.8 | −173.6 | −499.1 | 56.7 | 0.9 |
| oligo6 | 56.0 | −200.1 | −583.3 | 56.1 | 0.1 |
| oligo7 | 56.5 | −224.4 | −655.2 | 58.0 | 1.5 |
| oligo8 | 56.9 | −167.9 | −480.2 | 57.3 | 0.4 |
| oligo9 | 57.0 | −161.3 | −456.6 | 59.1 | 2.1 |
| oligo10 | 57.0 | −177.2 | −510.7 | 56.3 | 0.7 |
| oligo11 | 57.5 | −201.2 | −580.6 | 59.2 | 1.7 |
| oligo12 | 58.0 | −146.5 | −411.0 | 58.9 | 0.9 |
| oligo13 | 58.0 | −154.6 | −436.9 | 58.4 | 0.4 |
| oligo14 | 58.0 | −154.6 | −437.2 | 58.2 | 0.2 |
| oligo15 | 58.0 | −183.4 | −525.8 | 58.8 | 0.8 |
| oligo16 | 58.0 | −179.3 | −512.1 | 59.4 | 1.4 |
| oligo17 | 58.0 | −154.6 | −436.9 | 58.4 | 0.4 |
| oligo18 | 58.0 | −182.0 | −522.4 | 58.3 | 0.3 |
| oligo19 | 58.3 | −152.8 | −429.6 | 59.5 | 1.2 |
| oligo20 | 58.5 | −177.8 | −507.2 | 59.6 | 1.1 |
| oligo21 | 58.5 | −185.7 | −531.5 | 59.7 | 1.2 |
| oligo22 | 59.0 | −232.7 | −678.5 | 59.3 | 0.3 |
| oligo23 | 60.0 | −155.6 | −436.2 | 60.8 | 0.8 |
| oligo24 | 60.0 | −159.7 | −452.5 | 58.5 | 1.5 |
| oligo25 | 60.0 | −144.9 | −406.1 | 58.9 | 1.1 |
| oligo26 | 60.0 | −240.7 | −699.9 | 60.8 | 0.8 |
| oligo27 | 60.5 | −153.1 | −429.9 | 60.0 | 0.5 |
| oligo28 | 60.5 | −192.8 | −551.7 | 60.6 | 0.1 |
| oligo29 | 60.5 | −226.7 | −653.7 | 62.0 | 1.5 |
| oligo30 | 60.8 | −200.8 | −575.4 | 61.3 | 0.5 |
| oligo31 | 61.4 | −199.3 | −571.7 | 60.8 | 0.6 |
| oligo32 | 61.5 | −168.1 | −474.7 | 61.1 | 0.4 |
| oligo33 | 61.5 | −257.7 | −748.5 | 62.5 | 1.0 |
| oligo34 | 61.8 | −177.3 | −506.1 | 59.3 | 2.5 |
| oligo35 | 62.0 | −161.6 | −453.6 | 61.6 | 0.4 |
| oligo36 | 62.0 | −176.0 | −500.1 | 60.4 | 1.6 |
| oligo37 | 62.5 | −188.0 | −533.3 | 62.7 | 0.2 |
| oligo38 | 62.5 | −200.2 | −574.0 | 61.1 | 1.4 |
| oligo39 | 63.0 | −169.3 | −476.5 | 62.3 | 0.7 |
| oligo40 | 63.0 | −168.9 | −474.3 | 62.9 | 0.1 |
| oligo41 | 63.0 | −234.7 | −675.1 | 63.5 | 0.5 |
| oligo42 | 63.5 | −195.7 | −556.8 | 62.7 | 0.8 |
| oligo43 | 63.5 | −177.0 | −498.1 | 63.6 | 0.1 |
| oligo44 | 63.8 | −208.5 | −598.6 | 61.6 | 2.2 |
| oligo45 | 64.0 | −171.0 | −479.8 | 63.5 | 0.5 |
| oligo46 | 64.0 | −171.1 | −481.1 | 62.7 | 1.3 |
| oligo47 | 64.0 | −177.5 | −500.3 | 63.1 | 0.9 |
| oligo48 | 64.0 | −185.2 | −521.9 | 64.3 | 0.3 |
| oligo49 | 65.0 | −195.5 | −554.7 | 63.6 | 1.4 |
| oligo50 | 65.0 | −171.1 | −479.9 | 63.5 | 1.5 |
| oligo51 | 65.5 | −185.6 | −524.1 | 63.8 | 1.7 |
| oligo52 | 65.5 | −201.3 | −572.0 | 63.9 | 1.6 |
| oligo53 | 65.5 | −178.1 | −500.7 | 63.9 | 1.6 |
| oligo54 | 66.5 | −229.5 | −648.9 | 68.4 | 1.9 |
| oligo55 | 69.0 | −222.1 | −623.6 | 69.9 | 0.9 |
| oligo56 | 69.0 | −196.8 | −548.9 | 69.0 | 0.0 |
| oligo57 | 69.5 | −205.3 | −574.5 | 69.0 | 0.5 |
| oligo58 | 70.0 | −197.0 | −549.1 | 69.3 | 0.7 |
| Mean Absolute Error | | | | | 1.0 |
| Sum of Absolute Errors | | | | | 55.2 |
| Sum of Squared Errors | | | | | 74.2 |

(*rounded to the nearest tenth)

As shown in Table 11, the $T_m$s of the 58 oligonucleotides were predicted using Equation V-1, with the mean absolute error of 1.0, the sum of absolute error of 55.2, and the sum of squared error of 74.2.

The $T_m$ prediction performances of the four (4) equations were compared. As a result, it was found that the method using Equation V-1 including both the parameters α and β in addition to the NN parameters reduced the error between the experimental $T_m$ and the predicted $T_m$, thereby providing the most accurate predicted $T_m$.

Furthermore, for a sophisticated comparison between the equations for the $T_m$ prediction performance, the slope of the trend line and the coefficient of determination $R^2$ were determined in a scatter plot indicating the correlation between the experimental $T_m$ and the predicted $T_m$.

Figure 3A:
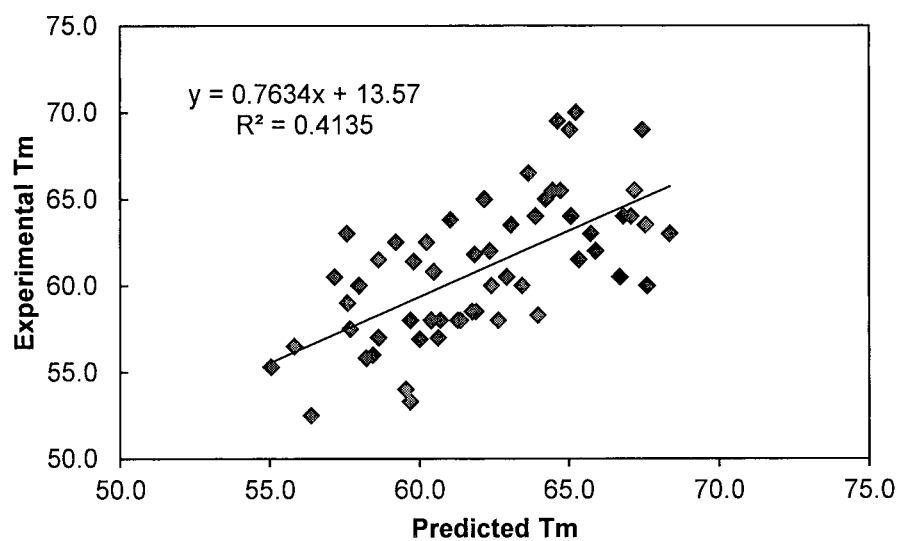
FIG. 3A shows (A) a scatter plot illustrating the correlation between the experimental $T_m$ and the predicted $T_m$ calculated using Equation I-1 and (B) a scatter plot illustrating the correlation between the experimental $T_m$ and the predicted $T_m$ calculated using Equation III-1.
Figure 3A:
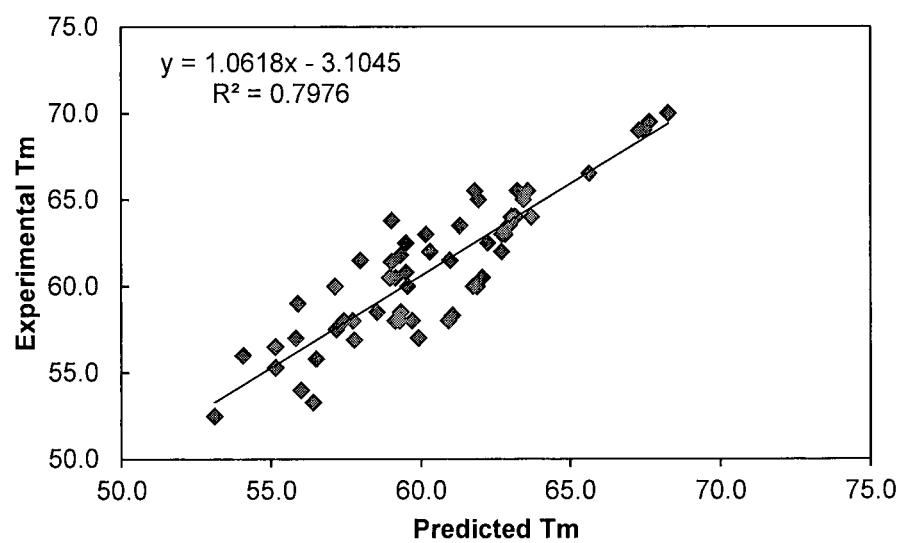
Figure 3B:
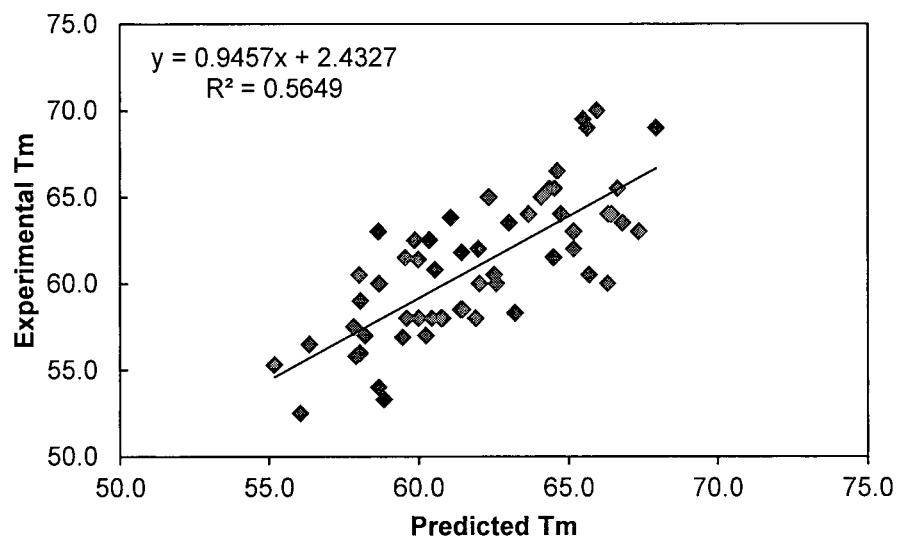
FIG. 3B shows (A) a scatter plot illustrating the correlation between the experimental $T_m$ and the predicted $T_m$ calculated using the Equation IV-1 and (B) a scatter plot illustrating the correlation between the experimental $T_m$ and the predicted $T_m$ calculated using the Equation V-1.
Figure 3B:
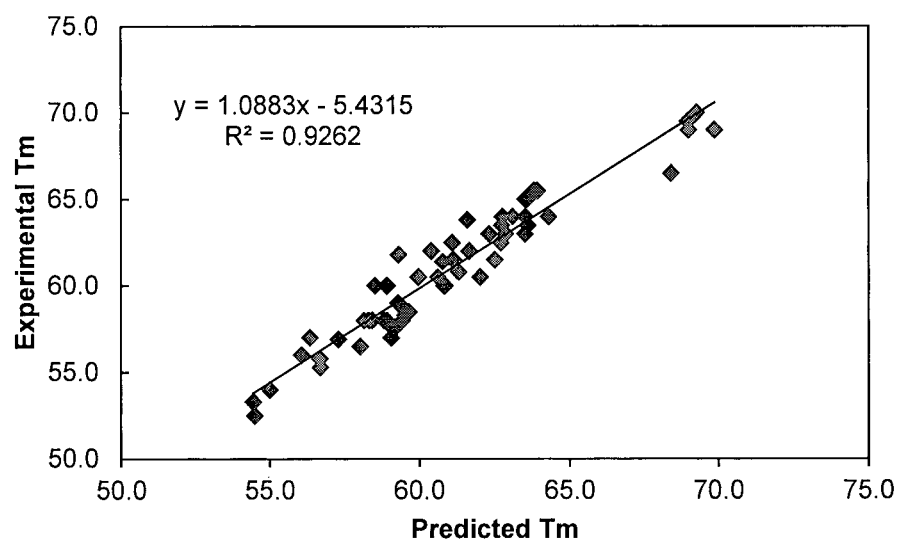

The results are shown in FIGS. 3A and 3B.

As shown in FIGS. 3A and 3B, it was found that the slope of the trend line in the scatter plot showing the correlation between the experimental $T_m$ and the predicted $T_m$ was 0.7634 for Equation I-1, 1.0618 for Equation III-1, 0.9457 for Equation IV-1, and 1.0883 for Equation V-1. Further, it was found that coefficient of determination $R^2$ was 0.4135 for Equation I-1, 0.7976 for Equation III-1, 0.5649 for Equation IV-1, and 0.9262 for Equation V-1.

The results demonstrate that using the equation including both the parameters α and β in addition to the NN parameters enables to obtain the predicted $T_m$ most similar to the experimental $T_m$.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for hybridizing a target nucleic acid sequence acid with an oligonucleotide of interest, comprising:
   (a) receiving a plurality of reference data sets, wherein the reference data set comprises (i) information about the sequences of a plurality of reference oligonucleotides such that each nearest-neighbor (NN) sequence occurs with the frequency of at least two and (ii) information about the experimental melting temperatures ($T_m$s) of the plurality of reference oligonucleotides in a defined reaction environment, wherein the plurality of reference data sets are generated in differently defined reaction environments;
   (b) establishing an equation for $T_m$ calculation for each of the differently defined reaction environments using each of the plurality of reference data sets including the information (i)-(ii); wherein the establishment of the equation comprises determining the values of NN thermodynamic parameters comprising the enthalpy change (ΔH) and the entropy change (ΔS), for each of NN sequences, wherein the values of the NN thermodynamic parameters determined are different for differently defined reaction environments;
   (c) calculating the $T_m$ of an oligonucleotide of interest in one among the differently defined reaction environments using the equation established for the one among the differently defined reaction environments;
   (d) providing the $T_m$ of an oligonucleotide of interest which is determined using the equation established for the one among the differently defined reaction environments, and
   (e) hybridizing the target nucleic acid sequence with the oligonucleotide of interest at a temperature using the $T_m$ calculated in step (c),
   wherein the $T_m$ calculated in step (c) is the $T_m$ of an oligonucleotide of interest in the one among the differently defined reaction environments.

2. The method of claim 1, wherein the equation for $T_m$ calculation is represented by Equation I:

$$Tm = \frac{\Delta H° \times m}{\Delta S°} - n \qquad \text{Equation I}$$

wherein $T_m$ is the melting temperature of the oligonucleotide; $\Delta H°$ is the sum of the enthalpy changes; $\Delta S°$ is the sum of the entropy changes; and m and n are constants.

3. The method of claim 2, wherein m is 1000 and n is 273.15.

4. The method of claim 1, wherein the equation for Tm calculation comprises the parameters of the enthalpy change ($\Delta H$) and the entropy change ($\Delta S$) for each of nearest-neighbor (NN) sequences, and one or more additional parameters.

5. The method of claim 4, wherein the one or more additional parameters comprise a parameter for correction of entropy change and/or a parameter for correction of Tm contribution by length of the oligonucleotide.

6. The method of claim 1, wherein the equation for $T_m$ calculation is represented by Equation V:

$$Tm = \frac{\Delta H° \times m}{\Delta S° + \alpha} + \beta \ln(\text{length}) - n \qquad \text{Equation V}$$

wherein $T_m$ is the melting temperature of the oligonucleotide; $\Delta H°$ is the sum of the enthalpy changes; $\Delta S°$ is the sum of the entropy changes; $\alpha$ is a first additional parameter for correction of entropy change; $\beta$ is a second additional parameter for correction of $T_m$ contribution by length of the oligonucleotide; length is the length of the oligonucleotide; and m and n are constants.

7. The method of claim 6, wherein m is 1000 and n is 273.15.

8. The method of claim 1, wherein the determination of the values of the parameters in step (b) is performed by linear regression or nonlinear regression.

9. The method of claim 1, wherein the determination of the values of the parameters in step (b) is performed by least square method.

* * * * *